(12) United States Patent
Isaacs et al.

(10) Patent No.: US 8,328,834 B2
(45) Date of Patent: Dec. 11, 2012

(54) ULTRASONIC DEVICE FOR CUTTING AND COAGULATING

(75) Inventors: Karen K. Isaacs, Burlington, KY (US); Michael R. Lamping, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 530 days.

(21) Appl. No.: 12/248,262

(22) Filed: Oct. 9, 2008

(65) Prior Publication Data

US 2009/0099582 A1 Apr. 16, 2009

Related U.S. Application Data

(60) Provisional application No. 60/978,883, filed on Oct. 10, 2007.

(51) Int. Cl.
*A61B 17/32* (2006.01)

(52) U.S. Cl. .......................... 606/169; 604/22

(58) Field of Classification Search .................. 606/167, 606/169, 170; 600/50, 459; 604/22
See application file for complete search history.

(56) References Cited

U.S. PATENT DOCUMENTS

| | | | |
|---|---|---|---|
| 4,783,997 A | 11/1988 | Lynnworth | |
| 4,838,853 A | 6/1989 | Parisi | |
| 5,059,210 A | 10/1991 | Clark et al. | |
| 5,096,532 A | 3/1992 | Neuwirth et al. | |
| 5,112,300 A | 5/1992 | Ureche | |
| 5,322,055 A | 6/1994 | Davison et al. | |
| 5,527,273 A | 6/1996 | Manna et al. | |
| 5,630,420 A | 5/1997 | Vaitekunas | |
| 5,776,155 A | 7/1998 | Beaupre et al. | |
| 5,873,873 A | 2/1999 | Smith et al. | |
| 5,938,633 A | 8/1999 | Beaupre | |
| 6,056,735 A | 5/2000 | Okada et al. | |
| 6,063,098 A | 5/2000 | Houser et al. | |
| 6,278,218 B1 | 8/2001 | Madan et al. | |
| 6,325,811 B1 | 12/2001 | Messerly | |
| 6,425,907 B1 | 7/2002 | Shibata et al. | |
| 6,443,968 B1 | 9/2002 | Holthaus et al. | |
| 6,623,500 B1 | 9/2003 | Cook et al. | |
| 6,660,017 B2 | 12/2003 | Beaupre | |
| 6,719,776 B2 | 4/2004 | Baxter et al. | |
| 2002/0002378 A1 | 1/2002 | Messerly | |
| 2002/0049464 A1 | 4/2002 | Donofrio et al. | |
| 2002/0091404 A1 | 7/2002 | Beaupre | |
| 2002/0156493 A1 | 10/2002 | Houser et al. | |
| 2002/0183774 A1 | 12/2002 | Witt et al. | |
| 2003/0216766 A1 | 11/2003 | Wiener et al. | |

(Continued)

FOREIGN PATENT DOCUMENTS

FR 2454351 A1 11/1980

(Continued)

OTHER PUBLICATIONS

International Search Report dated Feb. 3, 2012; International Application No. 06825838.3.
International Search Report dated Jun. 4, 2012; International Application No. 06836314.2.

*Primary Examiner* — Victor Nguyen
(74) *Attorney, Agent, or Firm* — Verne E. Kreger, Jr.

(57) ABSTRACT

An ultrasonic clamp coagulator assembly that is configured to permit selective cutting, coagulation, and fine dissection required in fine and delicate surgical procedures. The assembly includes a housing, a curved blade assembly and a first shroud and a second shroud.

8 Claims, 38 Drawing Sheets

U.S. PATENT DOCUMENTS

| | | |
|---|---|---|
| 2004/0006269 A1 | 1/2004 | Novak et al. |
| 2004/0147946 A1 | 7/2004 | Mastri et al. |
| 2004/0193199 A1 | 9/2004 | Hashiguchi |
| 2004/0199194 A1* | 10/2004 | Witt et al. .................. 606/169 |
| 2004/0230214 A1 | 11/2004 | Donofrio et al. |
| 2004/0245893 A1 | 12/2004 | Li et al. |
| 2005/0234484 A1 | 10/2005 | Houser et al. |
| 2007/0191713 A1* | 8/2007 | Eichmann et al. ............ 600/471 |
| 2011/0238067 A1 | 9/2011 | Moses et al. |

FOREIGN PATENT DOCUMENTS

| | | |
|---|---|---|
| JP | 2001-170066 A | 6/2001 |
| WO | WO 00/62688 A1 | 10/2000 |
| WO | WO 03/039429 A2 | 5/2003 |
| WO | WO 2005/046737 A2 | 5/2005 |

\* cited by examiner

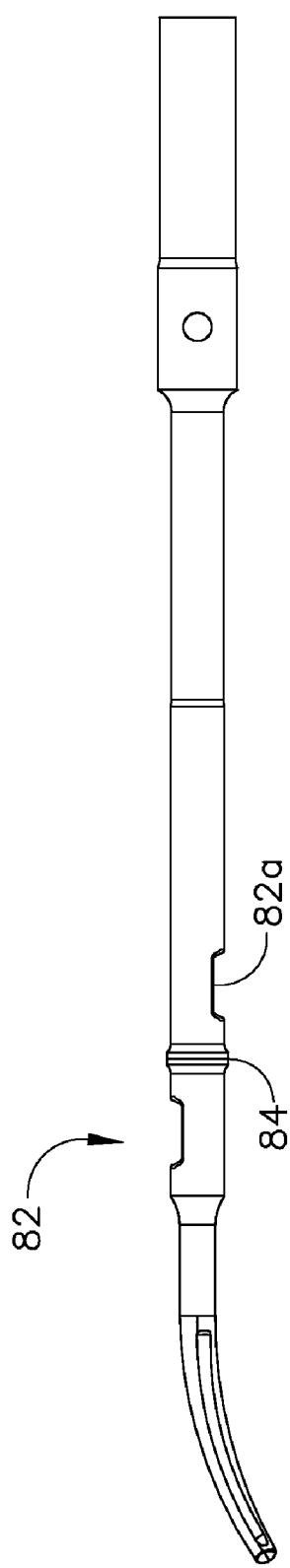
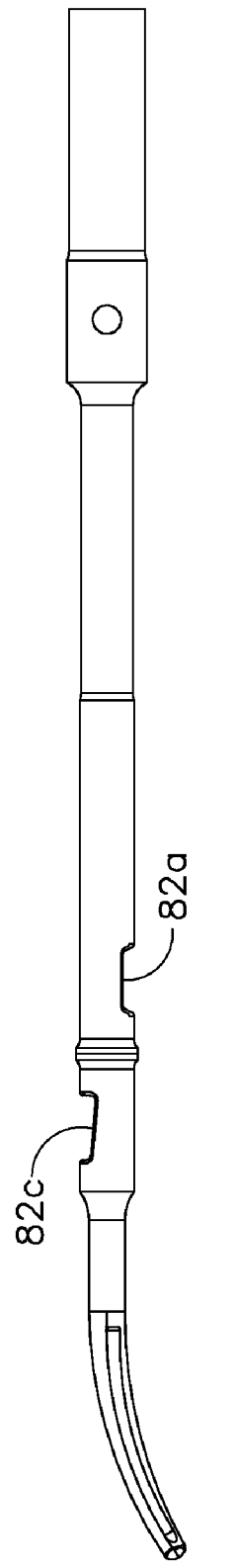
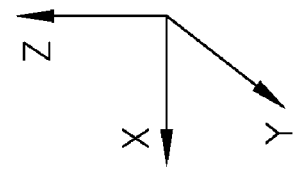

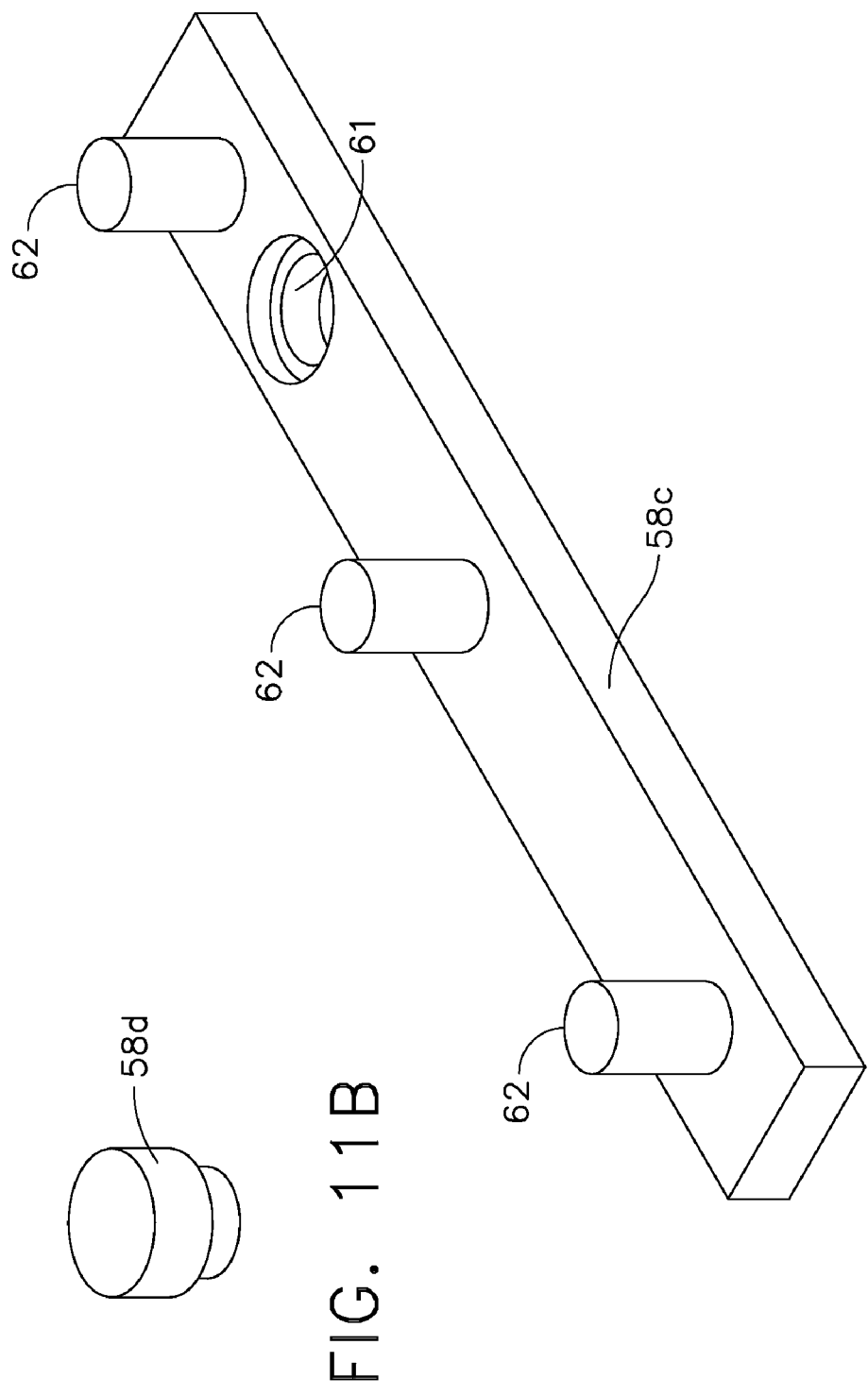

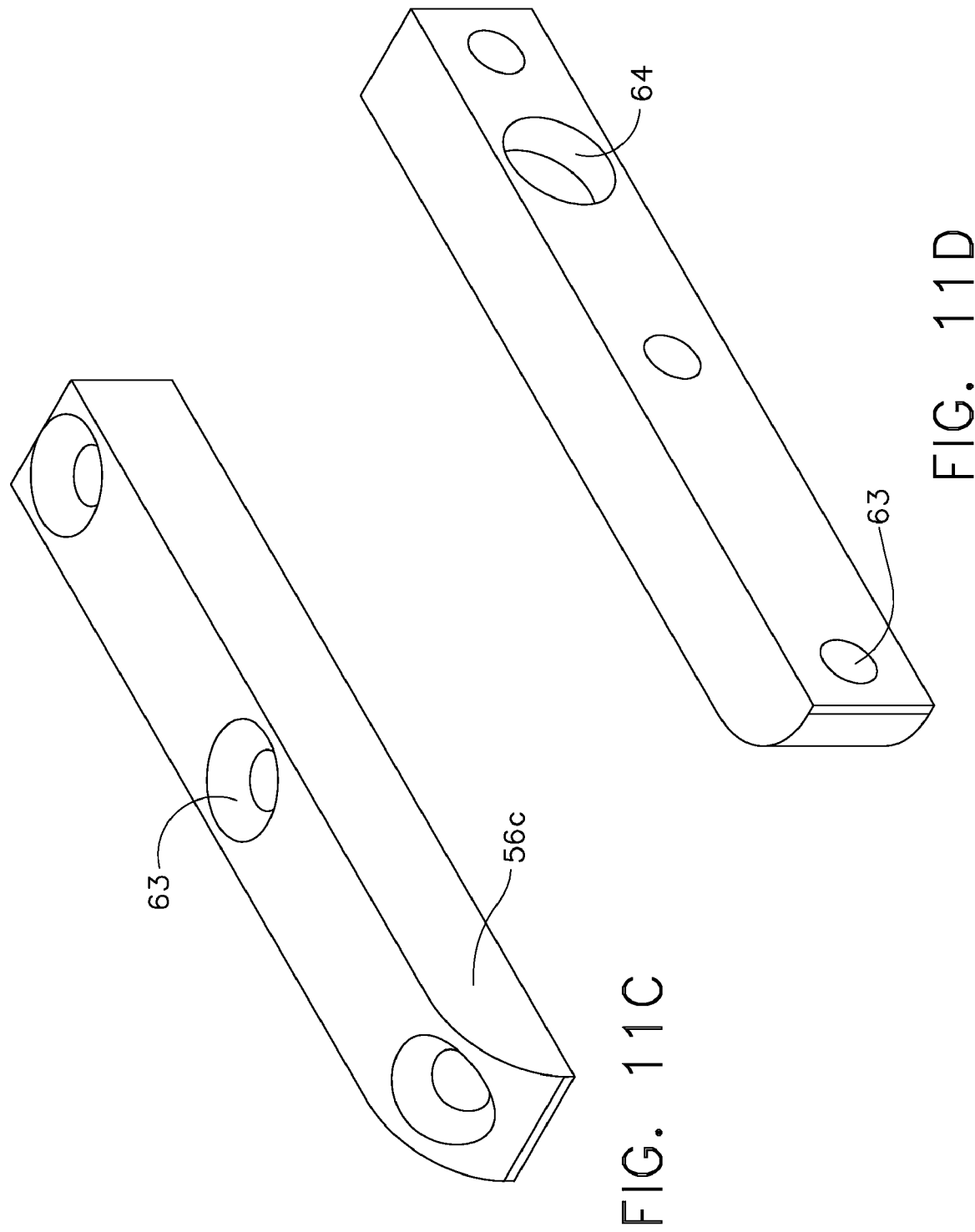

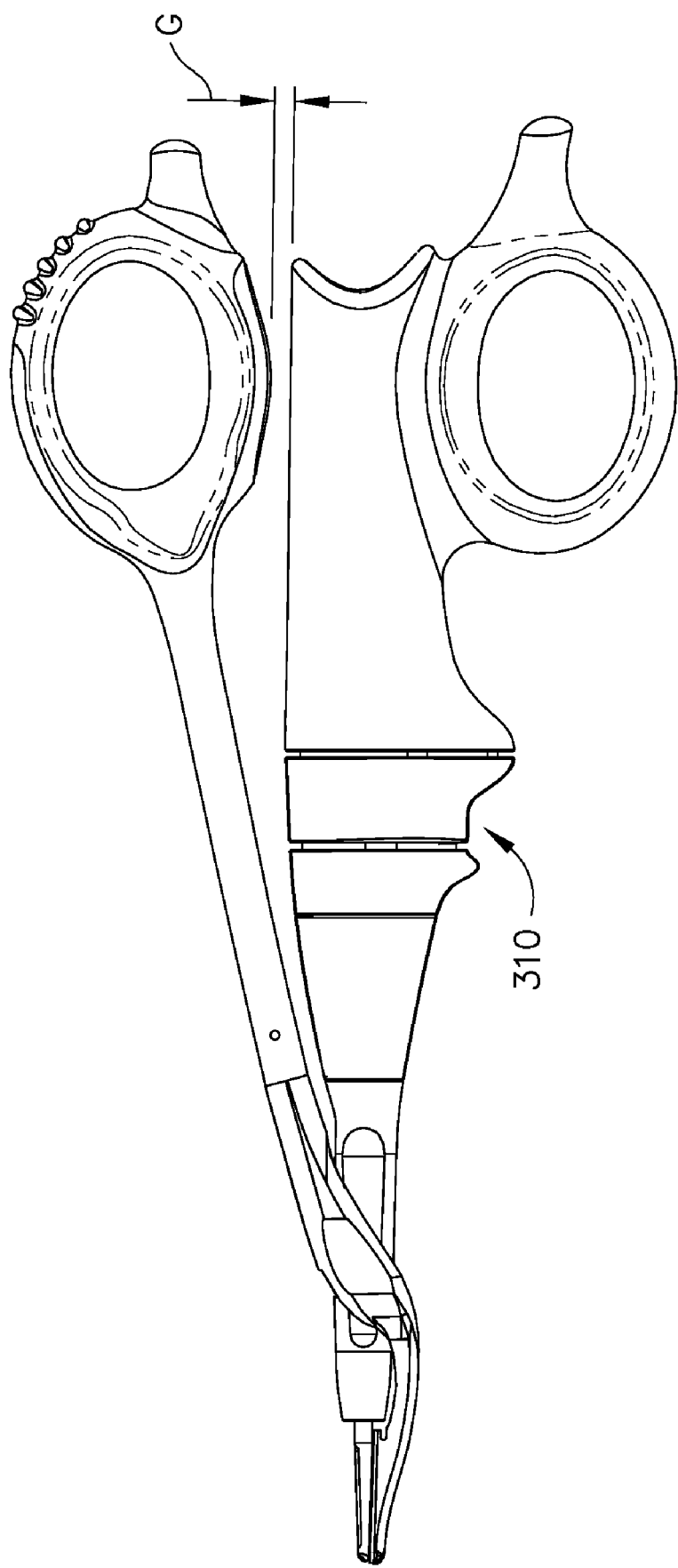

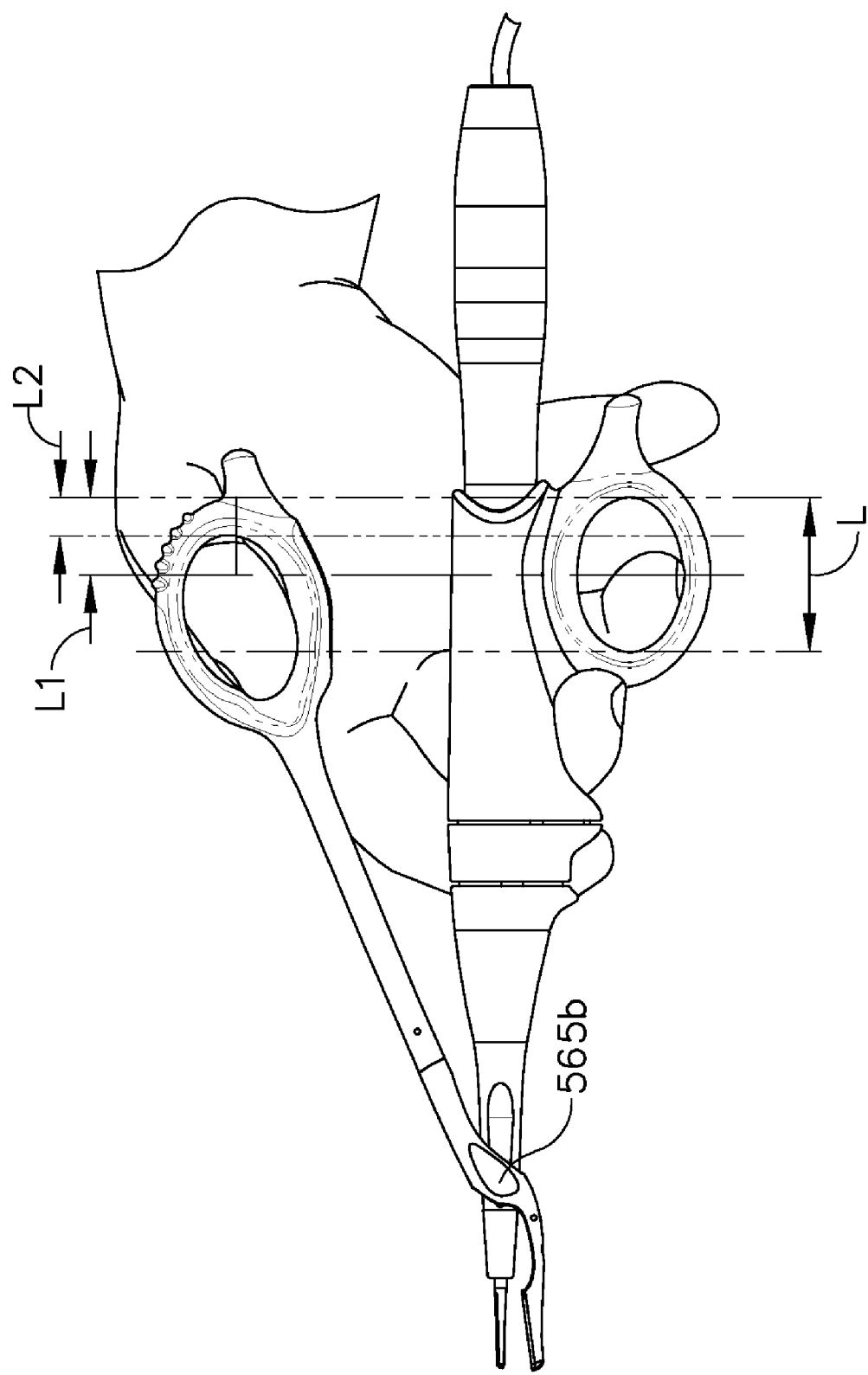

ULTRASONIC DEVICE FOR CUTTING AND COAGULATING

REFERENCE TO RELATED APPLICATIONS

The present application claims the priority benefit of U.S. provisional patent application Ser. No. 60/978,883, filed on Oct. 10, 2007.

FIELD OF THE INVENTION

The present invention generally relates to ultrasonic surgical systems and, more particularly, to an ultrasonic device that is optimized to allow surgeons to perform cutting, coagulation, and fine dissection required in fine and delicate surgical procedures such as a thyroidectomy.

BACKGROUND OF THE INVENTION

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and homeostasis by coagulation, desirably minimizing patient trauma. The cutting action is typically effected by an end-effector at the distal end of the instrument, which transmits ultrasonic energy to tissue brought into contact with the end-effector. Ultrasonic instruments of this nature can be configured for open surgical use, laparoscopic or endoscopic surgical procedures including robotic-assisted procedures.

Ultrasonic surgical instruments have been developed that include a clamp mechanism to press tissue against the blade of the end-effector in order to couple ultrasonic energy to the tissue of a patient. Such an arrangement (sometimes referred to as a clamp coagulator shears or an ultrasonic transector) is disclosed in U.S. Pat. Nos. 5,322,055; 5,873,873 and 6,325,811. The surgeon activates the clamp arm to press the clamp pad against the blade by squeezing on the handgrip or handle.

Some current designs of clamp coagulator shears utilize a foot pedal to energize the surgical instrument. The surgeon operates the foot pedal while simultaneously applying pressure to the handle to press tissue between the jaw and blade to activate a generator that provides energy that is transmitted to the cutting blade for cutting and coagulating tissue. Key drawbacks with this type of instrument activation include the loss of focus on the surgical field while the surgeon searches for the foot pedal, the foot pedal getting in the way of the surgeon's movement during a procedure and surgeon leg fatigue during long cases.

Various methods have been disclosed for curved end effector balancing, which include repositioning the mass along the end effector. The drawbacks of such methods are i) high stresses in the curved region, which makes the end effector more prone to fracture if it comes in contact with metal during surgery; ii) a shorter active length, which limits the vessel size that can be operated on, (the active length is defined as the length from the distal end of the blade to where the displacement is one half of the displacement at its distal end); and/or iii) the inability to separately balance orthogonal displacements.

Some current designs of clamp coagulator shears utilize handles that are either of a pistol or scissors grips design. The scissor grip designs may have one thumb or finger grip that is immovable and fixed to the housing and one movable thumb or finger grip. This type of grip may not be entirely familiar to surgeons who use other open-type surgical instruments, such as hemostats, where both thumb and finger grips move in opposition to one another. Current designs have scissor arms that rotate around a fixed pivot or rotation point that is perpendicular to the longitudinal axis of the working element. This approach is limited since the relative motion between the two arms is completely rotational. This feature limits the ability to control the pressure profile between the two working ends when fully closed.

Some current designs of clamp coagulator shears are not specifically designed for delicate procedures where precise dissection, cutting and coagulation are required. An exemplary procedure is a thyroidectomy where precise dissection, cutting and coagulation is required to avoid critical blood vessels and nerve bundles.

Some current designs of clamp coagulator shears have an uneven pressure profile across the blade with a higher pressure at the proximal end than the distal end for a given clamp force. An uneven pressure profile can affect the speed and completeness of tissue transaction, especially at the most distal tip of the blade.

Some current designs of clamp coagulator shears incorporate a spring in the handle mechanism to limit the amount of force applied to the blade by the clamp arm. A disadvantage of the spring limiting force mechanism is an increase in pad wear. As the device is used, the pad wears and a groove begins to form in the surface of the pad. This is prevalent in the abuse case where the device is activated when fully closed but with no tissue present between the blade and clamp pad. When the groove becomes deeper, a similar amount of force is placed on the blade due to the spring limit force feature. Therefore, the slope of the force vs. displacement curve is relatively flat.

It would be desirable to provide an ultrasonic surgical instrument that overcomes some of the deficiencies of current instruments. The ultrasonic surgical instrument described herein overcomes those deficiencies.

BRIEF SUMMARY OF THE INVENTION

An ultrasonic clamp coagulator assembly embodying the principles of the present invention is configured to permit selective dissection, cutting, coagulation and clamping of tissue during surgical procedures.

A first expression of a first embodiment of the invention is for an ultrasonic waveguide including an ultrasonically actuated blade attached to the distal end of the waveguide; a tissue pad having a tissue engaging surface having a first width and a second width less than the first width; and a clamp member defining a distal portion and a proximal portion and moveable with respect to the blade and having an open position in which at least a portion of the clamp member is spaced from the blade and a closed position in which the clamp member is adjacent to the blade for clamping tissue between the tissue pad and the blade.

A second expression of a first embodiment includes a clamp member defining a first dimension and a second dimension in a first plane and the first dimension is greater than the second dimension and further defining a first dimension and a second dimension in a second plane and the first dimension is greater than the second dimension.

A first expression of a third embodiment includes a method of assembling a sterilized ultrasonic clamp coagulator apparatus including the steps of providing an ultrasonic waveguide having a proximal end and a distal end and an ultrasonically actuated blade attached to the distal end of the waveguide; a tissue pad having a flange and a tissue engaging surface having a first width and a second width less than the first width; a clamp member moveable with respect to said end-effector and having an open position in which at least a portion of the clamp member is spaced from the blade and a closed position in which the clamp member is adjacent to the blade for clamping tissue between the tissue pad and the blade, and where the clamp member includes a slot for slidably receiving the flange and slidably engaging the flange within the slot and then sterilizing the clamp coagulator apparatus.

A first expression of a fourth embodiment of an ultrasonic surgical instrument is for a housing configured to accept a transducer and further defining a longitudinal axis; a first switch positioned on the housing for actuation by one or more fingers of a user in a direction parallel to the longitudinal axis and further electrically connected to a generator for providing an electrical signal to the generator for controlling a first level of ultrasonic energy delivered by the transducer.

A second expression of a fourth embodiment of an ultrasonic surgical instrument is for a second switch positioned on the housing for actuation by one or more fingers of a user in a direction parallel to the longitudinal axis and further electrically connected to a generator for providing an electrical signal to the generator for controlling a second level of ultrasonic energy delivered by the transducer.

A first expression of a fifth embodiment of an ultrasonic surgical instrument is for an ultrasonic waveguide defining a longitudinal axis, having a proximal end, a most distal node and a distal end and an ultrasonically actuated blade positioned at the distal end of the waveguide and which defines a functional asymmetry within a first plane, a first balance asymmetry distal to the most distal node and proximal to the blade; and a second balance asymmetry proximal to the most distal node.

A first expression of a sixth embodiment of an ultrasonic surgical instrument is for a housing, an outer shroud having a proximal end joined to the housing, an ultrasonic waveguide positioned within the outer tube, an ultrasonically actuated blade positioned at the distal end of the waveguide, and an actuating lever for operating a clamp arm located at the distal end of the lever. The actuating lever has camming members, which operatively engage the outer tube such that movement of the actuating lever positions the clamp arm between open and clamped positions relative to the blade.

A second expression of a sixth embodiment of an ultrasonic instrument is for stationary finger ring that defines an opening having a length L and the housing and a transducer are sized to position a center of gravity of the surgical instrument at the housing within the dimension of length L.

A first expression of a first embodiment of a torque wrench for use with an ultrasonic clamp coagulator apparatus is for a hand wrench body, a cantilever arm movably attached to said wrench body, at least one tooth located at the cantilever arm's distal end, and an adaptor rotatably attached to the hand wrench and comprising a cam for operatively engaging the tooth.

BRIEF DESCRIPTION OF THE FIGURES

The novel features of the invention are set forth with particularity in the appended claims. The invention itself, however, both as to organization and methods of operation, may best be understood by reference to the following description, taken in conjunction with the accompanying drawings in which:

FIG. 3C is an elevation view of an alternate embodiment of a waveguide and blade in accordance with the present invention;

FIG. 3D is an elevation view of an alternate embodiment of a waveguide and blade in accordance with the present invention;

FIG. 11A-B are an alternate expressions for a first and second tissue pad;

FIG. 11C is a perspective view of an alternate expression of a clamp arm for use with the tissue pads of FIGS. 11A-B;

FIG. 11D is an alternate view of the clamp are of FIG. 11C;

FIG. 16A is an elevation view of an ultrasonic instrument and pushbutton assembly in accordance with the present invention;

FIG. 18 is an elevation view of an ultrasonic instrument in accordance with the present invention as may be grasped by a user and defining a center of gravity;

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Further, unless otherwise indicated, the terms and expressions employed herein have been chosen for the purpose of describing the illustrative embodiments of the present invention for the convenience of the reader and are not for the purpose of limiting the invention.

Further, it is understood that any one or more of the following-described embodiments, expressions of embodiments, examples, etc. can be combined with any one or more of the other following-described embodiments, expressions of embodiments, examples, etc.

The present invention is particularly directed to an improved ultrasonic surgical clamp coagulator apparatus which is configured for effecting tissue cutting, coagulation, and/or clamping during surgical procedures, including delicate surgical procedures, such as a thyroidectomy. The present apparatus is configured for use in open surgical procedures. Versatile use is facilitated by selective use of ultrasonic energy. When ultrasonic components of the apparatus are inactive, tissue can be readily gripped and manipulated, as desired, without tissue cutting or damage. When the ultrasonic components are activated, the apparatus permits tissue to be gripped for coupling with the ultrasonic energy to effect tissue coagulation, with application of increased pressure efficiently effecting tissue cutting and coagulation. If desired, ultrasonic energy can be applied to tissue without use of the clamping mechanism of the apparatus by appropriate manipulation of the ultrasonic blade.

As will become apparent from the following description, the present clamp coagulator apparatus is particularly configured for disposable use by virtue of its straightforward construction. As such, it is contemplated that the apparatus be used in association with an ultrasonic generator unit of a surgical system, whereby ultrasonic energy from the generator unit provides the desired ultrasonic actuation for the present clamp coagulator apparatus. It will be appreciated that a clamp coagulator apparatus embodying the principles of the present invention can be configured for non-disposable or multiple use, and non-detachably integrated with an associated ultrasonic generator unit. However, detachable connection of the present clamp coagulator apparatus with an associated ultrasonic generator unit is presently preferred for single-patient use of the apparatus.

Figure 1:
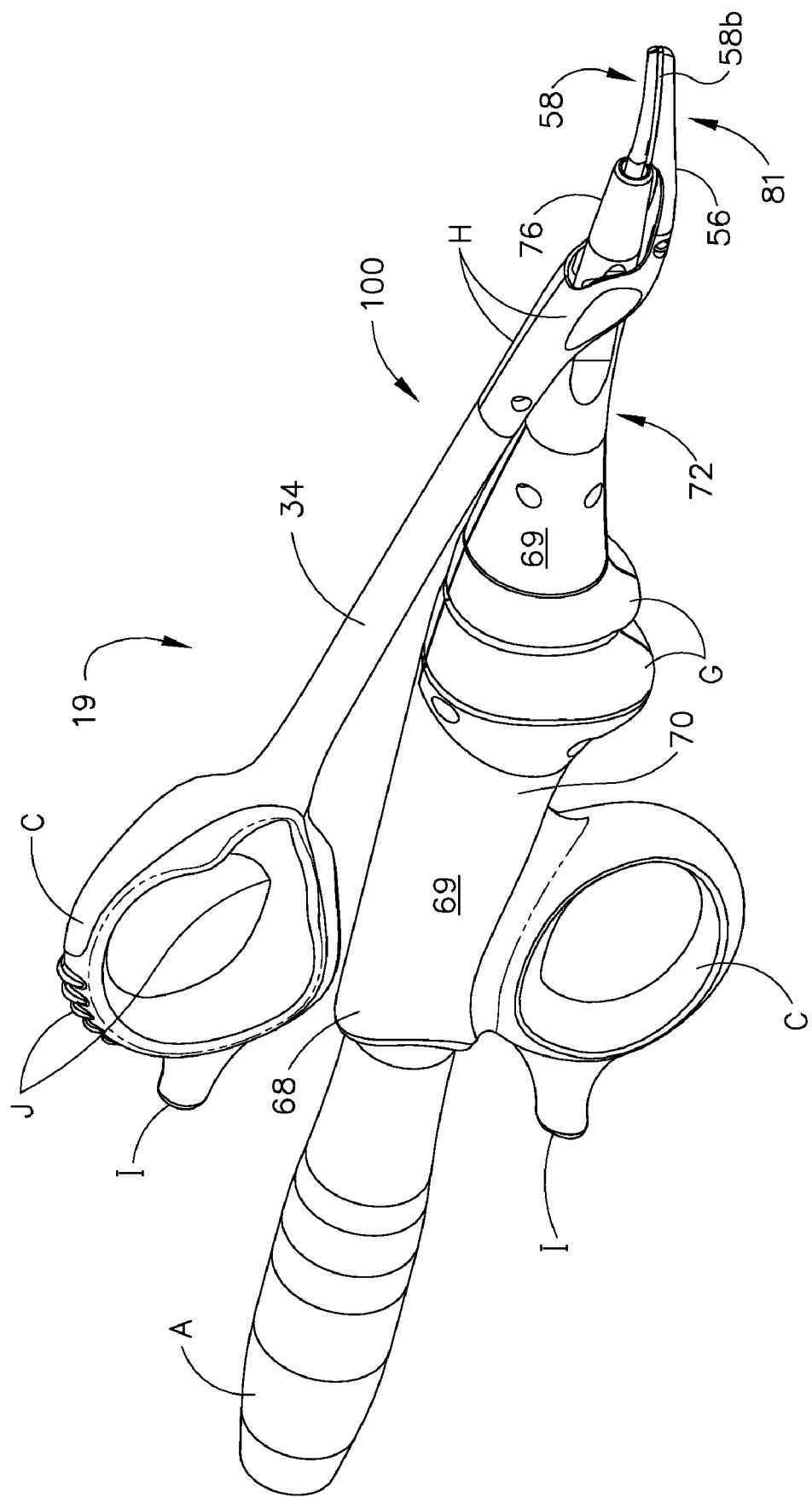
FIG. 1 is a perspective view illustrating an embodiment of an ultrasonic surgical instrument in accordance with the present invention.
Figure 2:
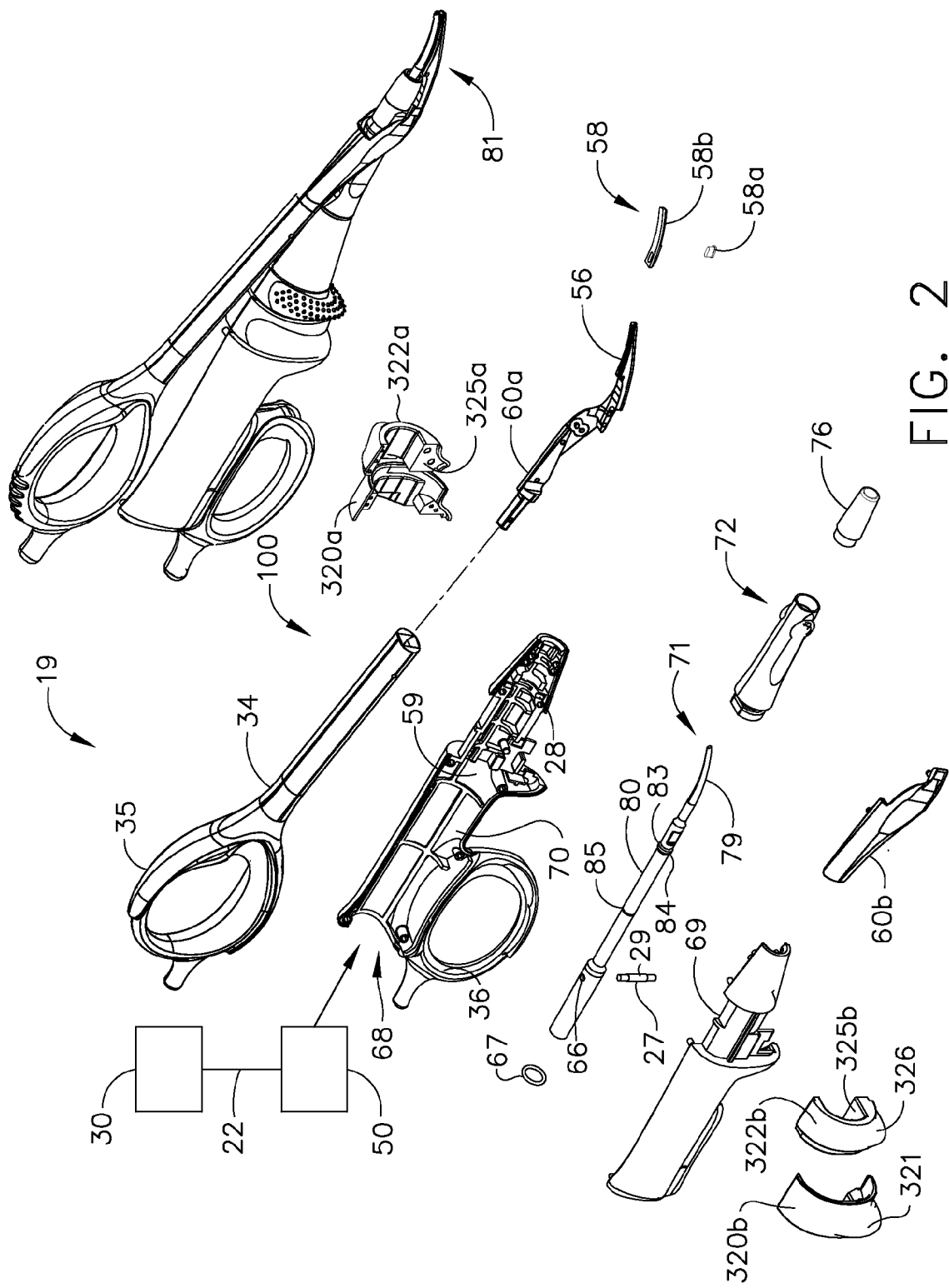
FIG. 2 is a perspective assembly view of FIG. 1.

With specific reference now to FIGS. 1 and 2, an embodiment of a surgical system 19, including an ultrasonic surgical instrument 100 in accordance with the present invention is illustrated. The surgical system 19 includes an ultrasonic generator 30 connected to an ultrasonic transducer 50 via cable 22, and an ultrasonic surgical instrument 100. It will be noted that, in some applications, the ultrasonic transducer 50 is referred to as a "hand piece assembly" because the surgical instrument of the surgical system 19 is configured such that a surgeon may grasp and manipulate the ultrasonic transducer 50 during various procedures and operations. A suitable generator is the GEN04 (also referred to as Generator 300) sold by Ethicon Endo-Surgery, Inc. of Cincinnati, Ohio. A suitable transducer is disclosed in co-pending U.S. patent application filed on Oct. 10, 2006, Ser. No. 11/545,784, entitled MEDICAL ULTRASOUND SYSTEM AND HANDPIECE AND METHODS FOR MAKING AND TUNING, the contents which are incorporated by reference herein.

Ultrasonic transducer 50, and an ultrasonic waveguide 80 together provide an acoustic assembly of the present surgical system 19, with the acoustic assembly providing ultrasonic energy for surgical procedures when powered by generator 30. The acoustic assembly of surgical instrument 100 generally includes a first acoustic portion and a second acoustic portion. In the present embodiment, the first acoustic portion comprises the ultrasonically active portions of ultrasonic transducer 50, and the second acoustic portion comprises the ultrasonically active portions of transmission assembly 71.

Further, in the present embodiment, the distal end of the first acoustic portion is operatively coupled to the proximal end of the second acoustic portion by, for example, a threaded connection.

The ultrasonic surgical instrument 100 includes a multi-piece handle assembly 68 adapted to isolate the operator from the vibrations of the acoustic assembly contained within transducer 50. The handle assembly 68 can be shaped to be held by a user in a conventional manner, but it is contemplated that the present ultrasonic surgical instrument 100 principally be grasped and manipulated in a scissor-like arrangement provided by a handle assembly of the instrument, as will be described. While multi-piece handle assembly 68 is illustrated, the handle assembly 68 may comprise a single or unitary component. The proximal end of the ultrasonic surgical instrument 100 receives and is fitted to the distal end of the ultrasonic transducer 50 by insertion of the transducer into the handle assembly 68. The ultrasonic surgical instrument 100 may be attached to and removed from the ultrasonic transducer 50 as a unit. The ultrasonic surgical instrument 100 may include a handle assembly 68, comprising mating housing portions 69 and 70 and an ultrasonic transmission assembly 71. The elongated transmission assembly 71 of the ultrasonic surgical instrument 100 extends orthogonally from the instrument handle assembly 68.

The handle assembly 68 may be constructed from a durable plastic, such as polycarbonate or a liquid crystal polymer. It is also contemplated that the handle assembly 68 may alternatively be made from a variety of materials including other plastics, ceramics or metals. Traditional unfilled thermoplastics, however, have a thermal conductivity of only about 0.20 W/m° K (Watt/meter-° Kelvin). In order to improve heat dissipation from the instrument, the handle assembly may be constructed from heat conducting thermoplastics, such as high heat resistant resins liquid crystal polymer (LCP), Polyphenylene Sulfide (PPS), Polyetheretherketone (PEEK) and Polysulfone having thermal conductivity in the range of 20-100 W/m° K. PEEK resin is a thermoplastics filled with aluminum nitride or boron nitride, which are not electrically conductive. The thermally conductive resin helps to manage the heat within smaller instruments.

The transmission assembly 71 includes a waveguide 80 and a blade 79. It will be noted that, in some applications, the transmission assembly is sometimes referred to as a "blade assembly". The waveguide 80, which is adapted to transmit ultrasonic energy from transducer 50 to the tip of blade 79 may be flexible, semi-flexible or rigid. The waveguide 80 may also be configured to amplify the mechanical vibrations transmitted through the waveguide 80 to the blade 79 as is well known in the art. The waveguide 80 may further have features to control the gain of the longitudinal vibration along the waveguide 80 and features to tune the waveguide 80 to the resonant frequency of the system. In particular, waveguide 80 may have any suitable cross-sectional dimension. For example, the waveguide 80 may have a substantially uniform cross-section or the waveguide 80 may be tapered at various sections or may be tapered along its entire length.

Ultrasonic waveguide 80 may, for example, have a length substantially equal to an integral number of one-half system wavelengths (nλ/2). The ultrasonic waveguide 80 and blade 79 may be preferably fabricated from a solid core shaft constructed out of material, which propagates ultrasonic energy efficiently, such as titanium alloy (i.e., Ti-6Al-4V), aluminum alloys, sapphire, stainless steel or any other acoustically compatible material.

Ultrasonic waveguide 80 may further include at least one radial hole or aperture 66 extending therethrough, substantially perpendicular to the longitudinal axis of the waveguide 80. The aperture 66, which may be positioned at a node, is configured to receive a connector pin 27, discussed below, which connects the waveguide 80, to the handle assembly 70.

Blade 79 may be integral with the waveguide 80 and formed as a single unit. In an alternate expression of the current embodiment, blade 79 may be connected by a threaded connection, a welded joint, or other coupling mechanisms. The distal end of the blade 79 is disposed near an anti-node 85 in order to tune the acoustic assembly to a preferred resonant frequency $f_o$ when the acoustic assembly is not loaded by tissue. When ultrasonic transducer 50 is energized, the distal end of blade 79 or blade tip 79*a* is configured to move substantially longitudinally (along the x axis) in the range of, for example, approximately 10 to 500 microns peak-to-peak, and preferably in the range of about 20 to about 200 microns at a predetermined vibrational frequency $f_o$ of, for example, 55,500 Hz. Blade tip 79*a* also preferably vibrates in the y axis at about 1 to about 10 percent of the motion in the x axis.

The blade tip 79*a* provides a functional asymmetry or curved portion for improved visibility at the blade tip so that a surgeon can verify that the blade 79 extends across the structure being cut or coagulated. This is especially important in verifying margins for large blood vessels. The geometry also provides for improved tissue access by more closely replicating the curvature of biological structures. Blade 79 provides a multitude of edges and surfaces, designed to provide a multitude of tissue effects: clamped coagulation, clamped cutting, grasping, back-cutting, dissection, spot coagulation, tip penetration and tip scoring.

Blade tip 79*a* is commonly referred to as a functional asymmetry. That is, the blade (functionally, the blade provides a multitude of tissue effects) lies outside the longitudinal axis of waveguide 80 (that is, asymmetrical with the longitudinal axis), and accordingly creates an imbalance in the ultrasonic waveguide. If the imbalance is not corrected, then undesirable heat, noise, and compromised tissue effect occur.

It is possible to minimize unwanted tip excursion in the y and z axes, and therefore maximize efficiency with improved tissue effect, by providing one or more balance asymmetries or balancing features proximal to the blade functional asymmetry.

Referring now to FIGS. 3A-G, transmission assembly 71 includes one or more balancing features placed at blade 79, at a position proximal and/or distal to the distal most node 84. In addition, the balancing features at the waveguide 80 are shaped to balance the two orthogonal modes in the y and z axes, separately. The size and shape and location of the balance features allow flexibility to reduce stress at the blade 79, make the active length longer and separately balance the two orthogonal modes.

Figure 3A:
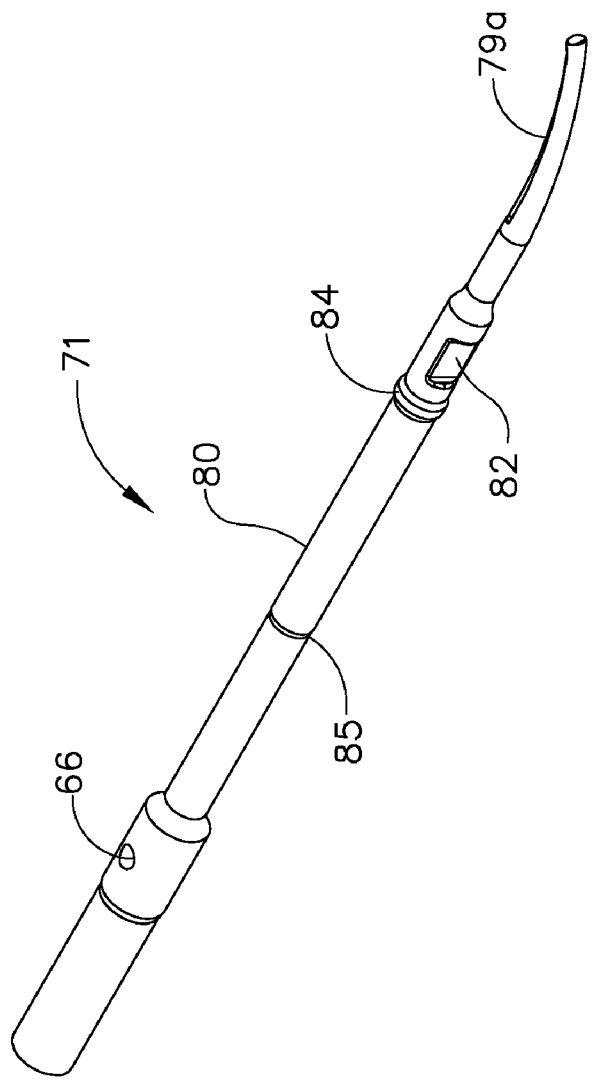
FIG. 3A is a perspective view of one embodiment of a waveguide and blade in accordance with the present invention.
Figure 3B:
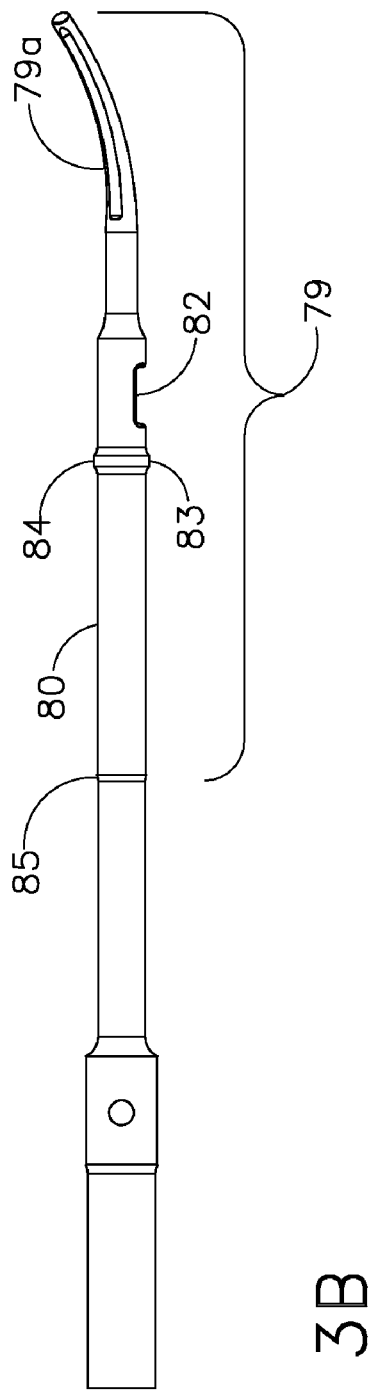
FIG. 3B is an elevation view of the waveguide and blade of FIG. 3A.

FIGS. 3A-B show a single balance cut 82 at the waveguide 80 distal to node 84. In this embodiment balance cut 82 has side walls perpendicular to the longitudinal axis of waveguide 80 and the bottom cut is parallel to the longitudinal axis of waveguide 80. In this embodiment the high stresses experienced during operation are localized at the balancing cut 82, which is away from the more sensitive curved region at the blade 79.

FIG. 3C shows two balancing features 82 and 82*a*, one distal and one proximal to the node 84. Adding second balance cut 82*a*, proximal to node 84 further eliminates the orthogonal bending modes thereby providing a more pure longitudinal motion (x direction) and removing the overlapping bending modes (y and z direction). Accordingly, the blade 79 is better balanced and has a longer active length.

FIG. 3D shows two balancing features 82c and 82a, distal and proximal to the node 84. An angled bottom cut at balance feature 82c allows individual balancing of the bending mode in the z direction.

Figure 3E:
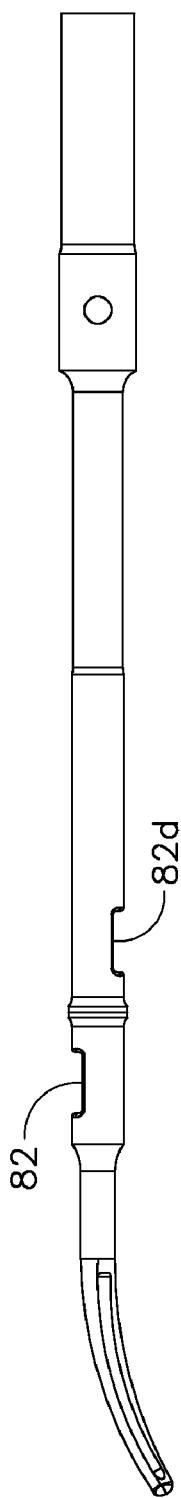
FIG. 3E is an elevation view of an alternate embodiment of a waveguide and blade in accordance with the present invention.
Figure 3F:
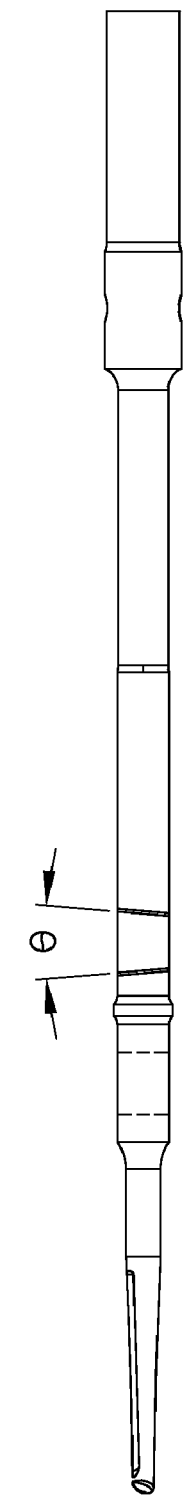
FIG. 3F is an alternate view of the embodiment of the waveguide and blade of FIG. 3E.

FIGS. 3E-F show two balancing features 82 and 82d, distal and proximal to the node 84. The side walls of balance feature 82d are angled with respect to each other in the x-z plane and provide for individual balancing of the bending mode in the y direction. The angled side walls define an included angle θ of between 1° and about 90°, preferably between about 15° and about 25°, and more preferably between about 19° and about 21°. The weight removed at each balance feature is a function of multiple parameters including the radius of curvature at blade tip 79a and the desired level of removal of the overlapping bending modes in the y and z direction. In an illustrative example, the balance cut 82 represents a weight reduction of about 0.003 to about 0.004 oz., and most preferably about 0.0034 oz. The balance cut 82d represents a weight reduction of about 0.004 to about 0.005 oz., and most preferably about 0.0043 oz.

Figure 3G:
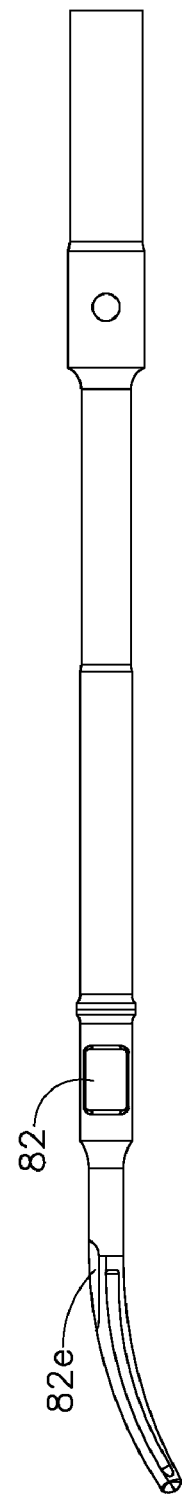
FIG. 3G is an elevation view of an alternate embodiment of a waveguide and blade in accordance with the present invention.

FIG. 3G shows one balance cut 82e in the curved blade region in addition to balance feature 82, distal to node 84. Balance cut 82e allows for balancing as well as improved acoustic performance as a result of wide frequency separation of transverse modes from the fundamental frequency, which is the longitudinal mode frequency.

As would be apparent to one skilled in the art, any combination of balance cuts 82 through 82e are possible to provide balancing of a waveguide and curved blade.

Figure 4:
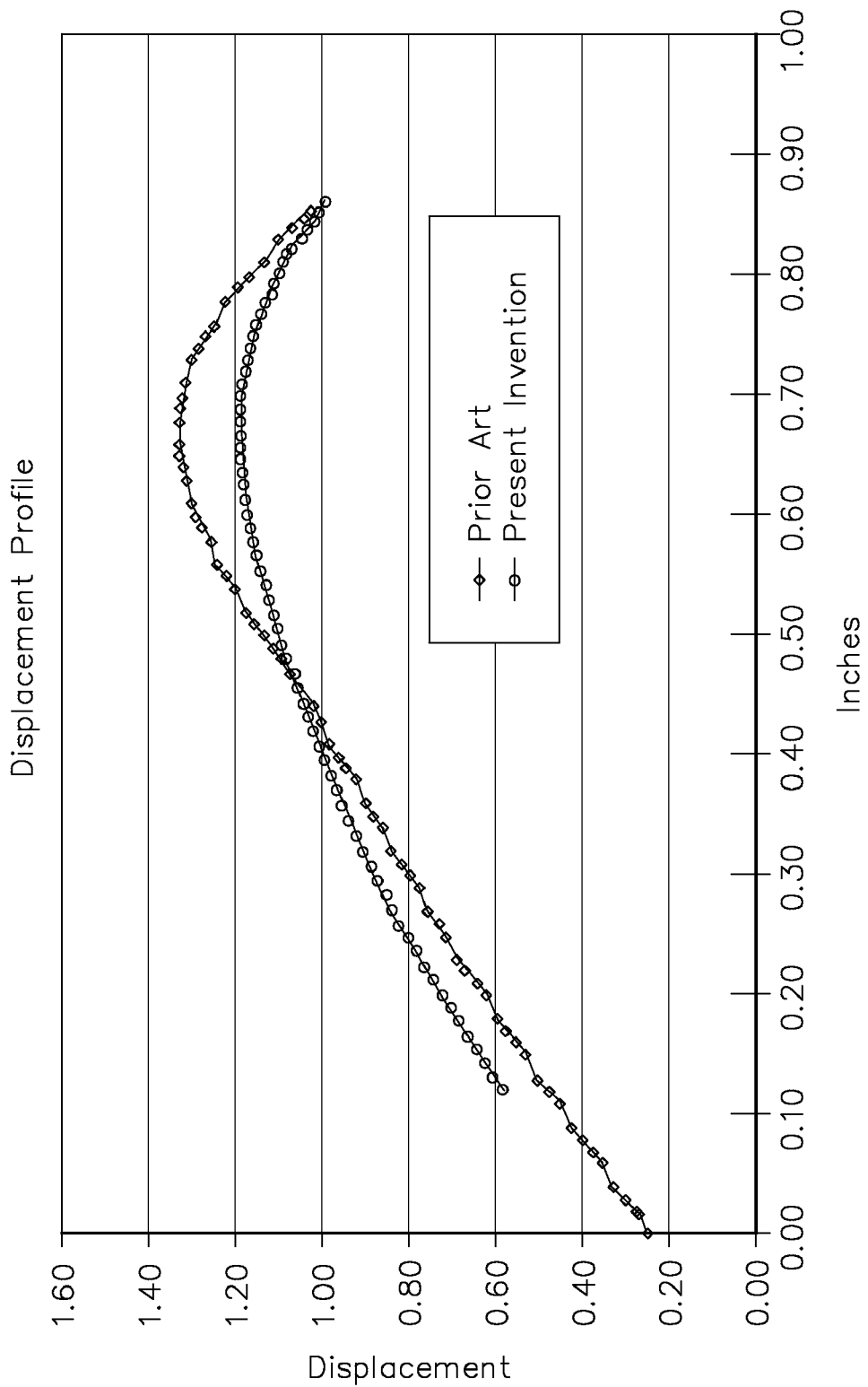
FIG. 4 is a graph illustrating the displacement profile of the present invention and the prior art.

FIG. 4 shows that the profile produced by the balancing cut features of FIG. 3E produces a 1.3 mm longer active length along the longitudinal displacement direction than is available from an LCS-C5 ultrasonic clamp coagulator, sold by Ethicon Endo-Surgery, Inc. (where the y axis is representative of the ratio between the displacement anywhere along blade tip 79a and the displacement at the most distal end of blade tip 79a). A longer active length is desirable for cutting and coagulating large vessels, for example, 5-7 mm vessels.

Figure 5:
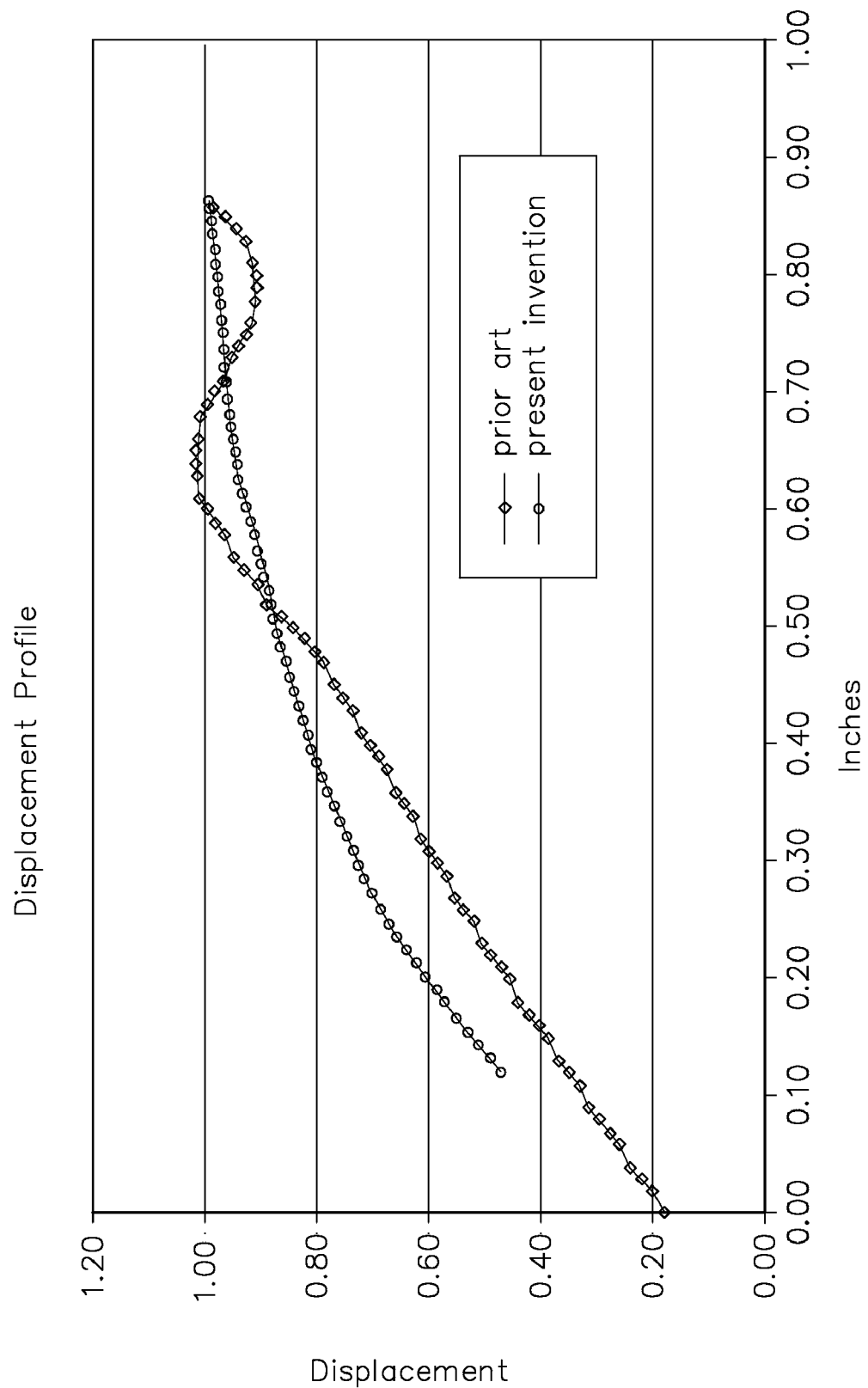
FIG. 5 is a graph illustrating an alternate displacement profile of the present invention and the prior art.

FIG. 5 shows that the profile produced by the balancing features of FIG. 3E produces a 2.5 mm longer active length (along the vector sum of displacements in the x, y and z directions) than is available from an LCS-C5 ultrasonic clamp coagulator, which is desirable for cutting and coagulating large vessels, for example, 5-7 mm vessels.

Referring back to FIGS. 1 and 2 an outer tubular member or outer shroud 72 attaches to the most proximal end of handle assembly 70. Attached to the distal end of the outer shroud 72 is a distal shroud 76. Both the outer shroud 72 and distal shroud 76 may attach via a snap fit, press fit, glue or other mechanical means. Extending distally from the distal shroud 76 is the end-effector 81, which comprises the blade 79 and clamp member 56, also commonly referred to as a jaw, in combination with one or more tissue pads 58. A seal 83 may be provided at the distal-most node 84, nearest the end-effector 81, to abate passage of tissue, blood, and other material in the region between the waveguide 80 and the distal shroud 76. Seal 83 may be of any known construction, such as an o-ring or silicon overmolded at node 84.

Referring now to FIGS. 6A-D and 7A-B, blade 79 is curved along with the associated clamp member 56. This is illustrative only, and blade 79 and a corresponding clamp member 56 may be of any shape as is known to the skilled artisan. One benefit of the invention, however, is the ability to perform finer, more delicate surgical procedures. It is also multifunctional and able to dissect tissue as well as coagulate and transect.

The ability to finely dissect is enabled primarily by the tapering of the end effector 81. The end effector is tapered in two planes, which mimics typical hemostats. This allows the user to create windows in the tissue and then spread the tissue apart more easily. The blade 79 and clamp member 56 are tapered in both the x and z directions from the proximal end to the distal end. The pad 58 is only tapered in the Z direction. That is, the clamp pad 58 has a constant thickness, but the width of the clamp pad 58 at the distal end is less than the width at the proximal end. Accordingly, the surface area of section A is greater than the surface area of section B.

In addition to the taper, the radius at the distal end of the blade 79 and clamp member 56 also promotes fine dissection. The radius at the tip of the clamp member 56 is approximately 0.040 inches, and the blade radius is approximately 0.045 inches.

Figure 6A:
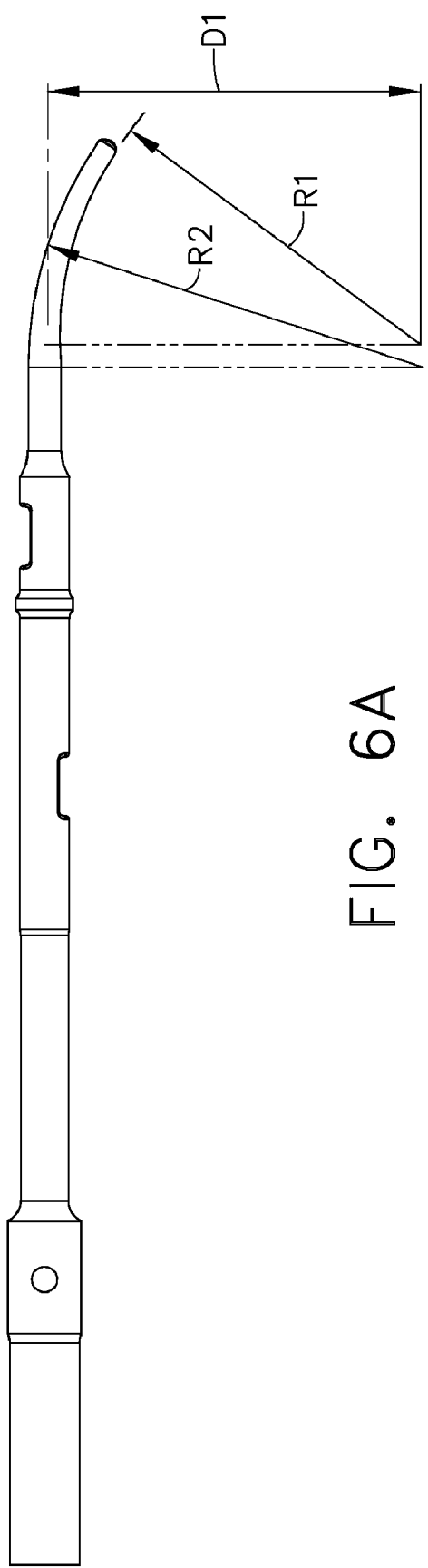
FIG. 6A is an elevation view of the waveguide and blade of FIGS. 3E-F illustrating one embodiment of the radius of curvature of the blade.

With specific reference to FIG. 6A, blade 79 is defined by an inside radius R1 and an outside radius R2 measured at a distance D1 from the longitundinal axis. The dimensions R1, R2 and D1 are selected in combination with the balance cuts previously discussed. In one embodiment R1 is from about 0.80 inches to about 1.00 inches and most preferably about 0.95 inches; R2 is from about 0.90 inches to about 1.10 inches and most preferably about 1.04 inches; and D1 is from about 0.90 inches to about 1.10 inches and most preferably about 0.99 inches.

Figure 6C:
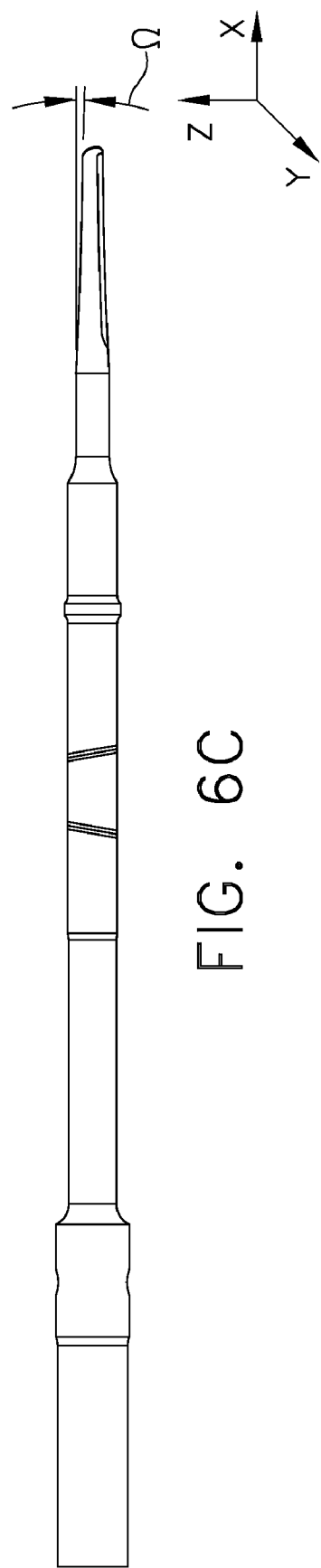
FIG. 6C is an alternate view of the embodiment of FIG. 6A.
Figure 6B:
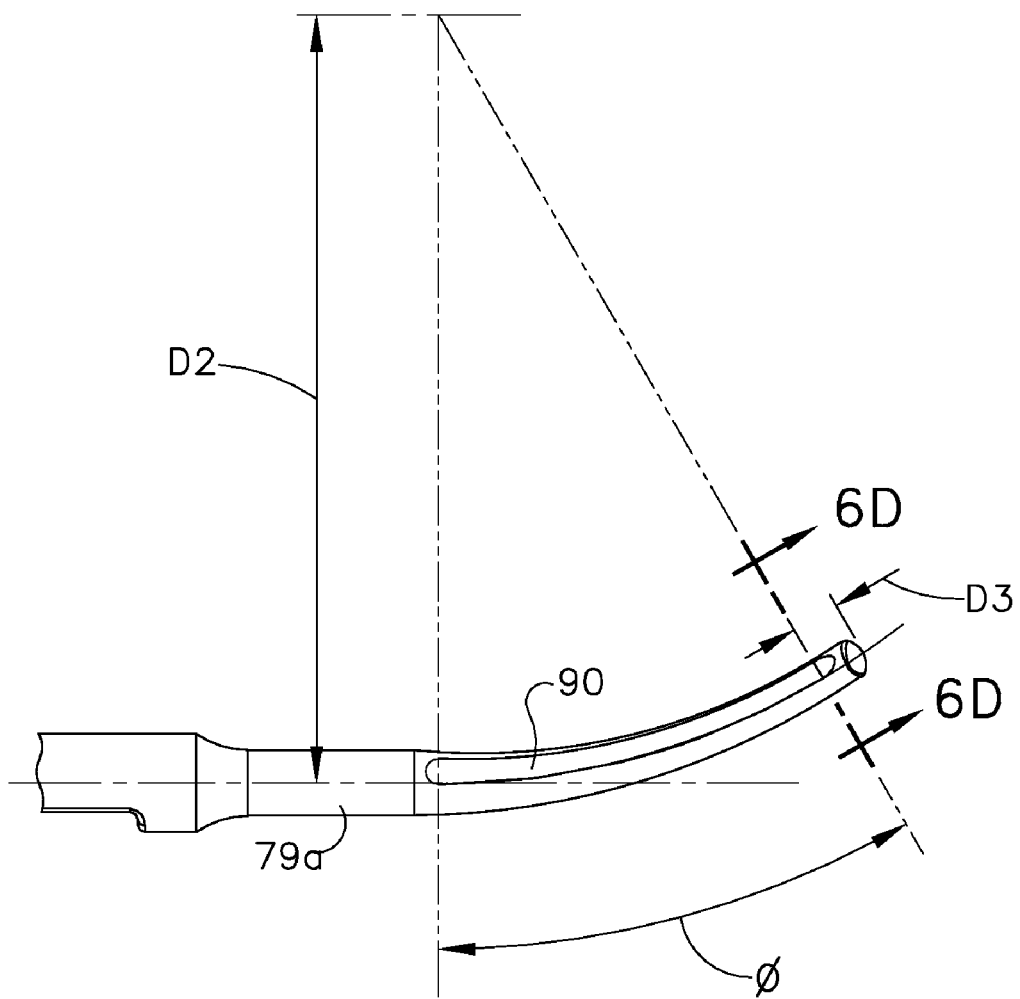
FIG. 6B is an exploded view of one embodiment of the blade of FIG. 6A and a radius cut.
Figure 6D:
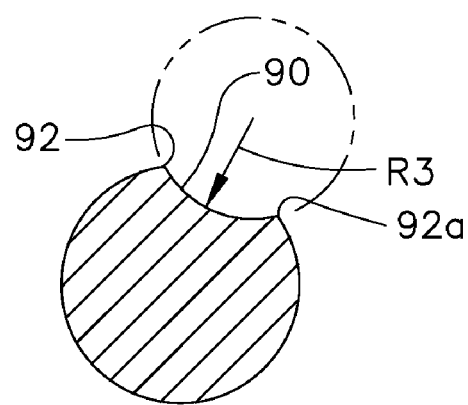
FIG. 6D is a section view of the embodiment of FIG. 6B.

FIGS. 6B and 6D further illustrate a second expression of the blade 79. Illustrated is a radius cut 90 in blade 79 to provide two back cutting edges 92 and 92a. As will be appreciated by the skilled artisan, radius cut 90 also provides a balance asymmetry within the functional symmetry to help balance the orthogonal modes. The back cutting edges 92 and 92a are positioned opposite the clamp pad 58 (FIG. 7B) to allow the surgeon to perform tissue cutting procedures without the assistance of the clamp pad 58. Preferably, the radius cut is distal to the most distal tip of blade 79 to allow for a blunt radius tip for tissue dissection as discussed above. In one example of the second expression of blade 79, a radius cut R3 is swept across an angle φ measured at a distance D2 from the longitudinal axis and starting a distance D3 from the distal tip of blade 79. In one embodiment R3 is from about 0.030 inches to about 0.060 inches and most preferably about 0.050 inches; angle φ is from about 20° to about 35° and most preferably about 30°; D2 is about 0.90 inches to about 1.10 inches and most preferably about 0.99 inches; and D3 is from about 0.085 inches to about 0.11 inches and most preferably about 0.09 inches.

Figure 7A:
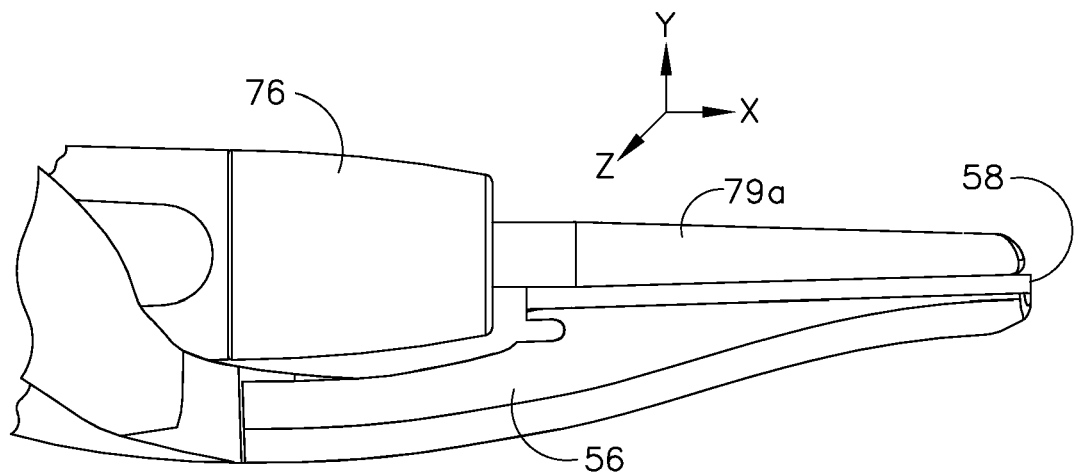
FIG. 7A is an elevation view of an end effector in accordance with the present invention.
Figure 7B:
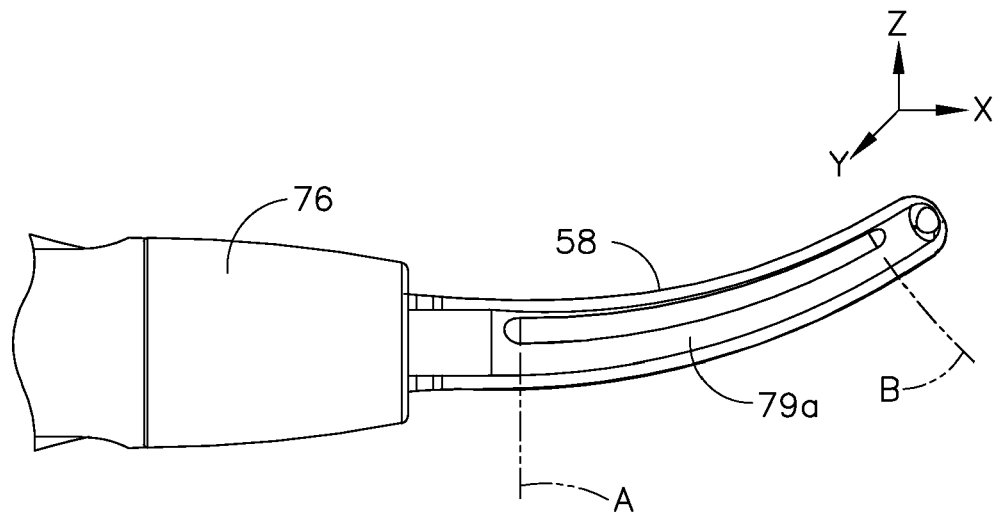
FIG. 7B is a plan view of the end effector of FIG. 7A.
Figure 8:
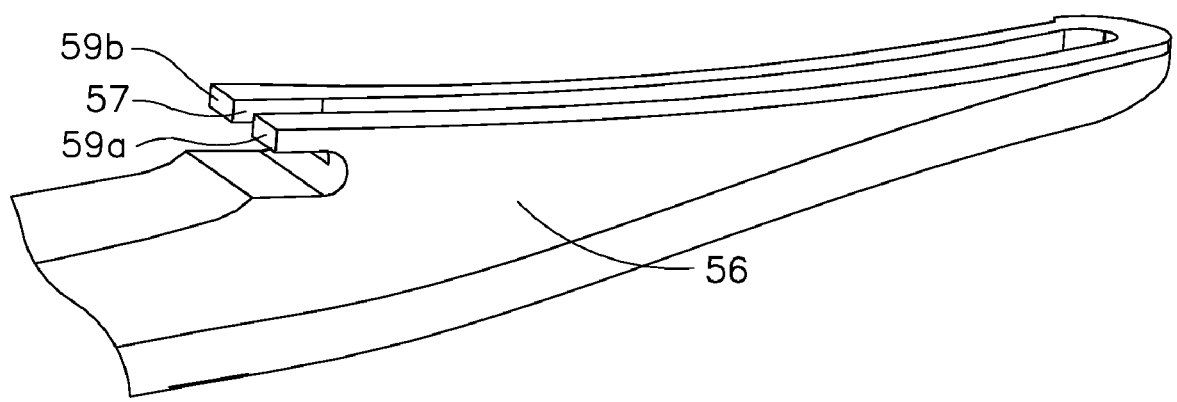
FIG. 8 is a perspective view from proximal to distal end of a clamp member in accordance with the present invention.
Figure 9A:
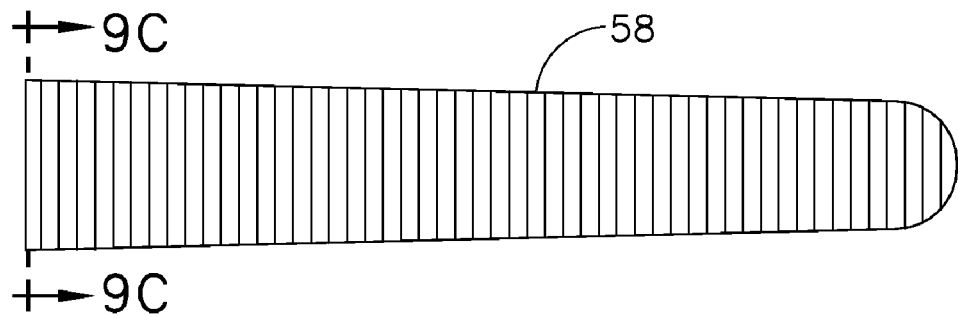
FIG. 9A is a plan view of a tissue pad in accordance with the present invention.
Figure 9B:
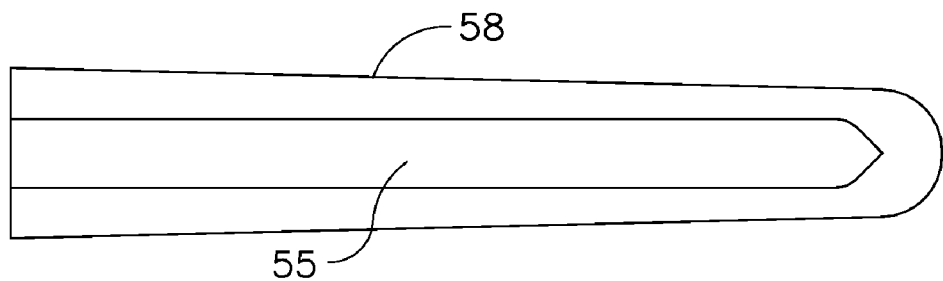
FIG. 9B is a plan view of the opposite face of the tissue pad of FIG. 9A.
Figure 9C:
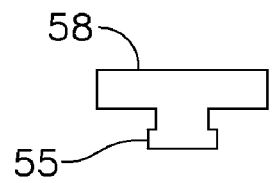
FIG. 9C is an elevation view the tissue pad of FIGS. 9A-B.

In a third expression of blade 79, FIG. 6C illustrates a taper defined by angle Ω relative to an axis parallel to the longitudinal axis of waveguide 80 from the proximal end of blade 79 to the distal end of blade 79. In one embodiment the taper may be on the blade surface that contacts tissue pad 58 (FIG. 7A). Alternatively, the taper may be the defined by the opposite surface comprising radius cut 90. Referring to FIG. 6C, angle Ω ranges from about 0.5° to about 5°, and preferably from about 1.5° to about 2°

Figure 15A:
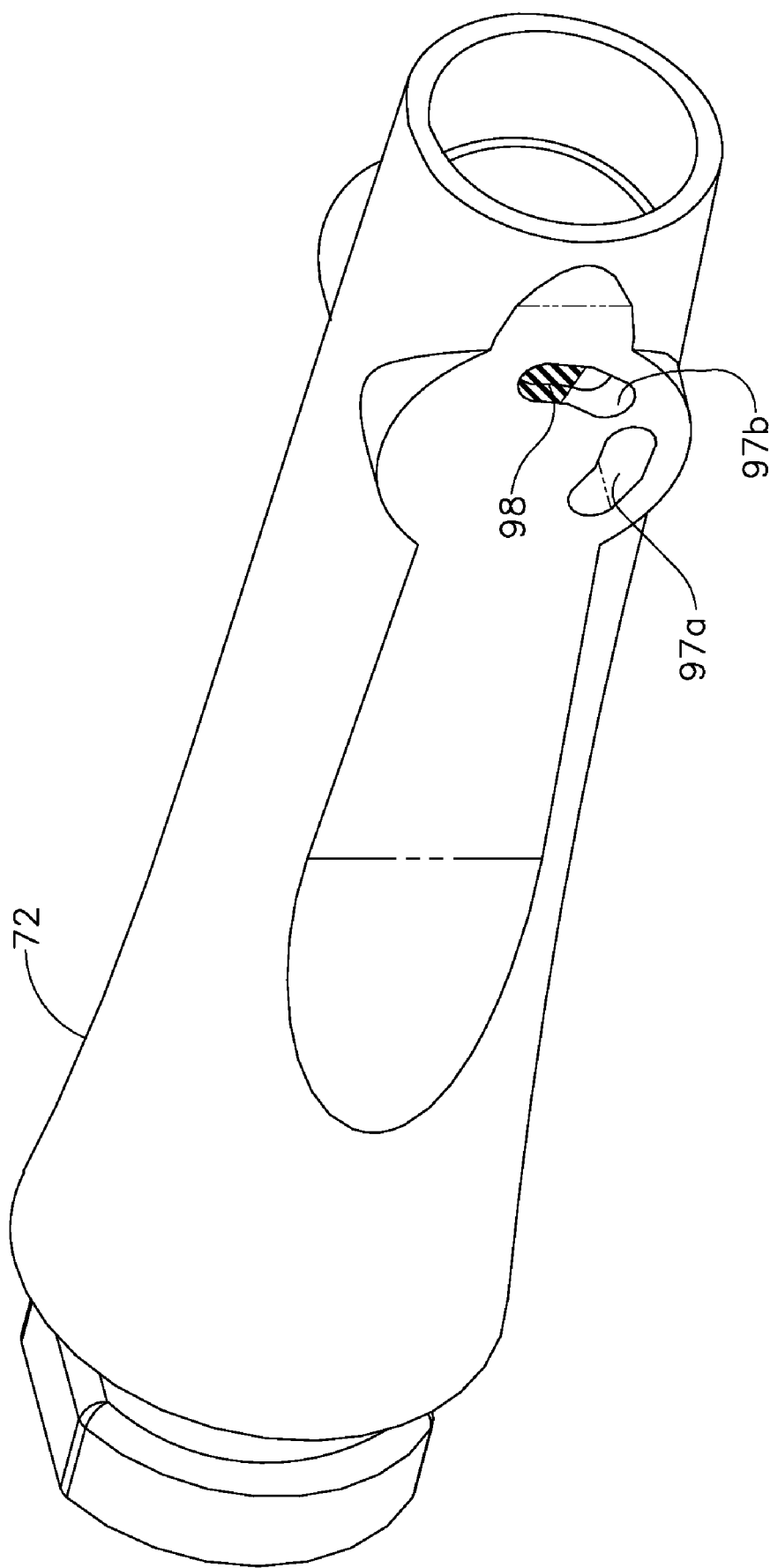
FIG. 15A is an exploded view of the outer shroud and cam slots.
Figure 15B:
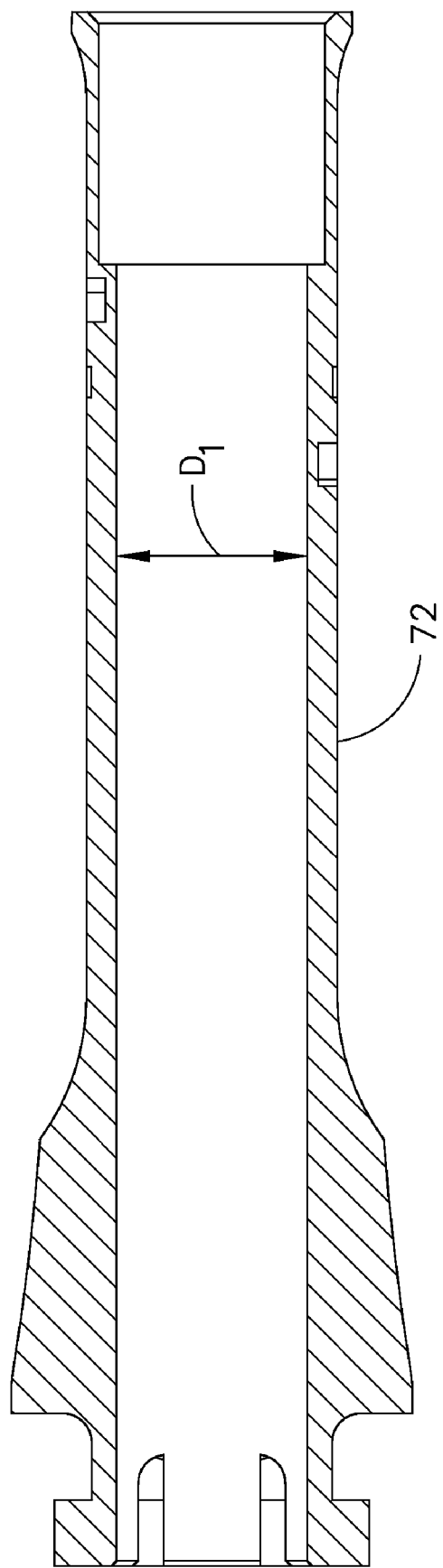
FIG. 15B is a cut away view of one embodiment of the outer shroud.

Referring now to FIG. 15B, due to the unique curvature of the blade tip 79a, it is preferable that the sheath covering the blade 79 is made in two pieces, outer shroud 72 and distal shroud 76, in order to maintain preferred inner dimensions of the distal shroud 76. The length of the outer shroud 72 and distal shroud 76 are critical because they allow passage of the blade during assembly. Preferably the inner diameter D1 of the outer shroud 72 is from about 0.175 inches to about 0.22 inches and most preferably about 0.197 inches. The length of the outer shroud 76 is between about 1.5 inches to about 2.4 inches. With a preferred inner diameter of about 0.197 inches, the maximum length of outer shroud 72 is about 2.311 inches.

Figure 15C:
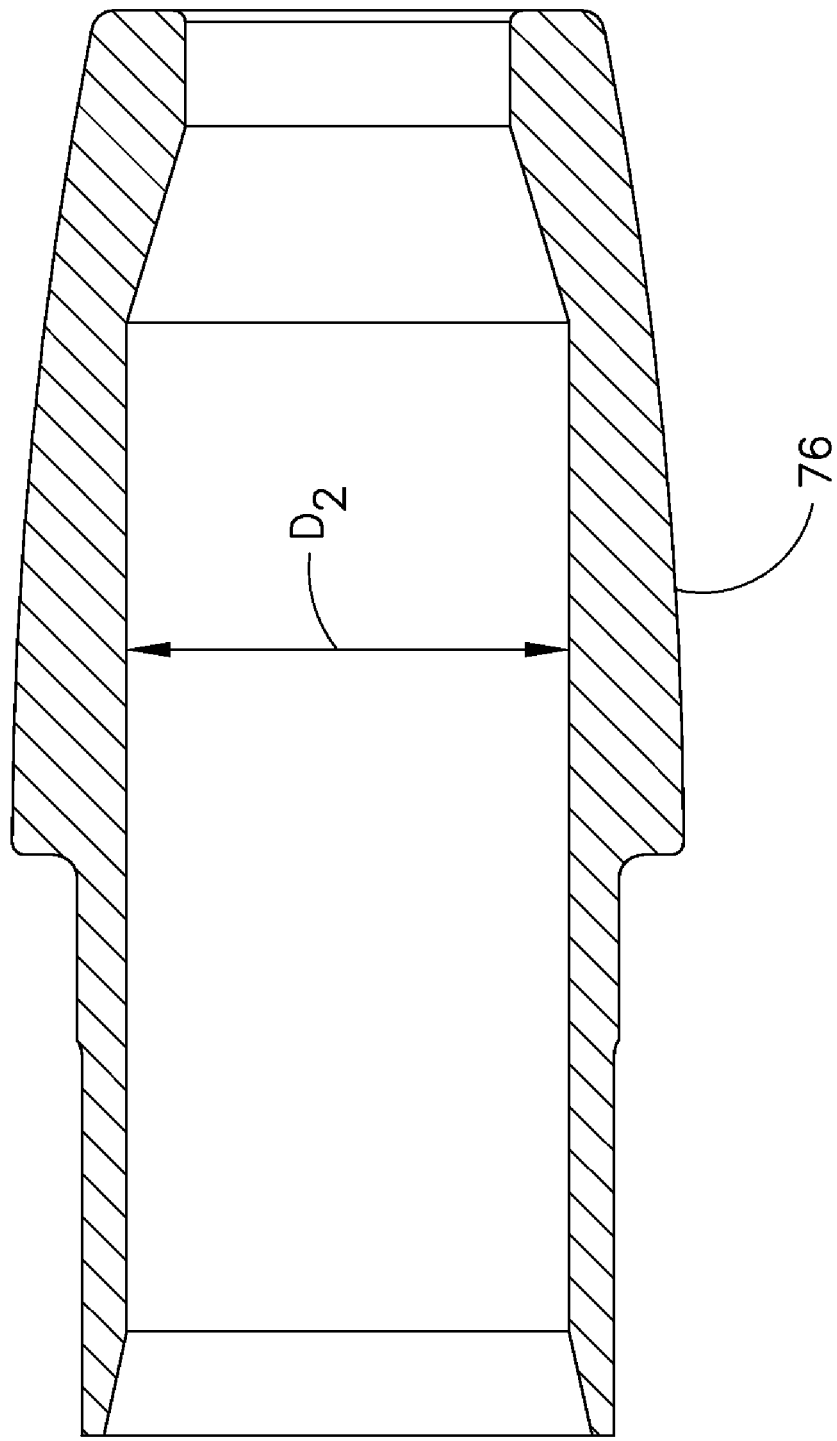
FIG. 15C is a cut away view of one embodiment of the distal shroud.

Referring now to FIG. 15C, the distal shroud 76 has a critical inner diameter D2 of about 0.185 inches to about 0.20 inches and most preferably about 0.191 inches. This diameter mates with the overmold 84 of the blade 79. This interaction between the overmold 84 of the blade and the inner diameter of the distal shroud 76 performs two critical functions. First, the tight tolerance isolates the vibrating blade from the distal shroud 76 to avoid metal to metal contact. Second, the tight tolerance provides stiffness to the blade system. Stiffness of the blade system is critical in maintaining the appropriate clamp force of the instrument.

During assembly the outer shroud 72 is passed over the blade 79 and then the distal shroud 76 is passed over the curved portion of the blade 79*a*. The length of the distal shroud 76 allows the blade 79 to pass through the distal shroud 76. In order to accommodate a preferred embodiment of the blade 79 to pass through the inner diameter of the distal shroud 76, the length of distal shroud 76 is preferably from about 0.600 inches to about 0.650 inches, and most preferably 0.616 inches. Once the distal shroud 76 is pressed fit onto the outer shroud 72 (or other attachment means, such as glue or mechanical fastering) the overmold of the blade 84 is secured within the 0.191" inner diameter.

Referring back to FIG. 2, waveguide 80 is positioned within cavity 59 of handle assembly 68. In order to properly locate the waveguide 80 both axially and radially, pin 27 extends through opening 66 of waveguide 80 (located at a node) and engages channel 28 (formed by the mating of housing portions 69 and 70). Preferably pin 27 is made of any compatible metal, such as stainless steel or titanium or a durable plastic, such as polycarbonate or a liquid crystal polymer. In a first expression of one embodiment, pin 27 is partially coated with an elasto-meric material 30, such as silicon for that portion 29 of pin 27 that extends through waveguide 80 and uncoated for that portion of pin 27 that engages members 69 and 70. The silicone provides insulation from the vibrating blade throughout the length of hole 66. This enables high efficiency operation whereby minimal overheating is generated and maximum ultrasonic output power is available at the blade tip for cutting and coagulation. The lack of insulation allows pin 27 to be held firmly within handle assembly 68 due to the lack of insulation, which would provide deformation and movement if pin 27 were completely coated with an insulating material.

Referring now to FIGS. 8 and 9A-C a first expression of clamp member 56 has a shaped slot 57 for accepting one or more tissue pads. This configuration prevents mis-loading of the tissue pads and assures that the appropriate pad is loaded at the correct location within clamp member 56. For example clamp member 56 may comprise a T-shaped slot 57 to accept a T-shaped flange 55 of clamp pad 58. Two mechanical stops 59 and 59*a*, when depressed, engage the proximal end of clamp pad 58 to secure the clamp pad within clamp member 56. As would be appreciated by those skilled in the art, flanges and corresponding slots may have alternate shapes and sizes to secure the clamp pads to the clamp arm. The illustrated flange configurations shown are exemplary only and accommodate the particular clamp pad material of one embodiment, but the particular size and shape of the flange may vary, including, but not limited to, flanges of the same size and shape. For unitary tissue pads, the flange may be of one configuration. Further, other tab stops are possible and may include any of the multiple methods of mechanically attaching the clamp pads to the clamp arm, such as rivets, glue, press fit or any other fastening means well know to the artisan.

Figure 10A:
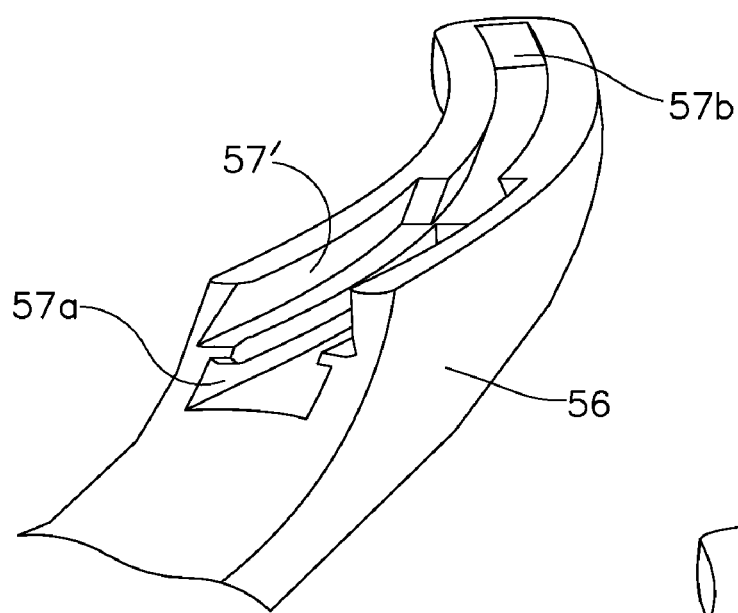
FIG. 10A is a perspective view of an alternate expression of the clamp member.
Figure 10B:
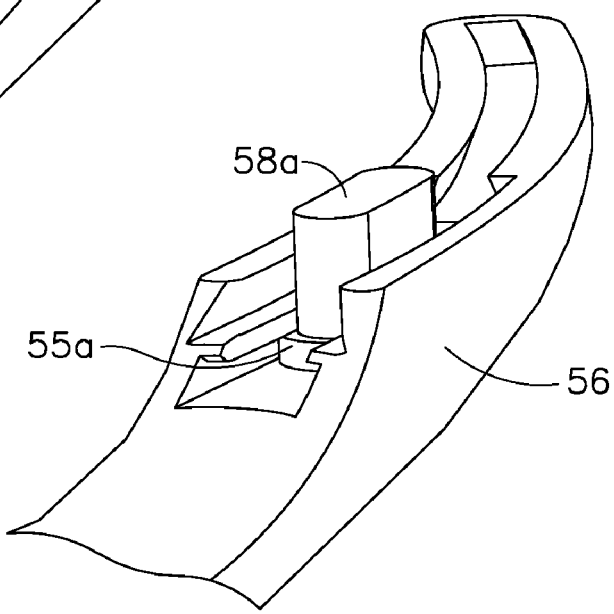
FIG. 10B is a perspective view of the clamp member of FIG. 10A and a first tissue pad.
Figure 10C:
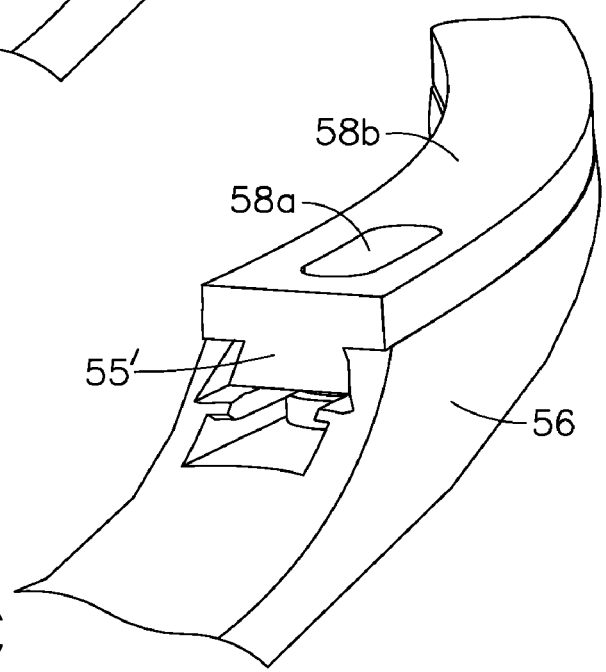
FIG. 10C is a perspective view of the clamp member of FIG. 10A and a first and second tissue pad.

Referring to FIGS. 10A-C, in a first expression of an alternate embodiment, clamp pad 58 consists of a first tissue pad 58*b* and a second pad portion 58*a*, which may be an insert within pad 58*b*. Tissue pad 58*b* may comprise a tissue engaging surface having saw tooth-like teeth and proximal portion 58*a* may have a smoother surface relative to pad 58*b*. The advantage of two separate components 58*a* and 58*b* is that each pad may be constructed from different materials. For example, having a two-piece tissue pad allows the use of a very lubricious material at the distal end that is not particularly resistant to high temperatures compared to a very high temperature material at the proximal end that is not particularly lubricious because the proximal end is an area of lower amplitude. Such a configuration matches the tissue pad materials to the amplitude of the blade 79.

In a second expression of an alternate embodiment of the present invention, clamp pad 58*b* is formed from TEFLON® or any other suitable low-friction material. Clamp pad 58*a* is formed from a base material and at least one filler material, which is a different material from the base material. The surface of proximal clamp pad 58*a* may be smoother than distal clamp pad 58*b*, or proximal clamp pad 58*a* may also have a similar type saw-tooth configuration.

Several benefits and advantages are obtained from one or more of the expressions of the invention. Having a tissue pad with a base material and at-least-one filler material allows the base material and the at-least-one filler material to be chosen with a different hardness, stiffness, lubricity, dynamic coefficient of friction, heat transfer coefficient, abradability, heat deflection temperature, glass transition temperature and/or melt temperature to improve the wearability of the tissue pad, which is important when high clamping forces are employed because tissue pads wear faster at higher clamping forces than at lower clamping forces. In experiments, a 15% graphite-filled polytetrafluoroethylene tissue pad showed substantially the same wear with a 7 pound clamping force as a 100% polytetrafluoroethylene tissue pad showed with a 1.5 pound clamping force. Having a flexible clamping arm and/or a flexible tissue pad should also improve the wearability of the tissue pad due to the ability of the flexible member to more evenly distribute the load across the entire surface of the tissue pad. Further benefits and expressions of this embodiment are disclosed in U.S. provisional patent application Ser. No. 60/548,301, filed on Feb. 27, 2004 and commonly assigned to the assignee of the present application.

In a third expression of an alternate embodiment, a tissue pad with a base material and at least two filler materials allows the base material and the at-least-two filler materials to be chosen with a different hardness, stiffness, lubricity, dynamic coefficient of friction, heat transfer coefficient, abradability, heat deflection temperature, and/or melt temperature to improve the wearability of the tissue pad, which is important when high clamping forces are employed because tissue pads wear faster at higher clamping forces than at lower clamping forces. In experiments, a 15% graphite-filled, 30% PTFE-filled polyimide tissue pad showed substantially the same or better wear with a 4.5 pound clamping force as a 100% polytetrafluoroethylene tissue pad showed with a 1.5 pound clamping force. The advantage of a 15% graphite-filled, 30% PTFE-filled polyimide tissue pad is increased heat resistance, which improves the overall wear resistance of the tissue pad. This polyimide-composite clamp pad has a useful heat resistance up about 800° F. to about 1200° F., as compared to a useful heat resistance up to about 660° F. of a PTFE clamp pad. Alternatively, Other materials are also useful for a portion of the tissue pad, such as ceramics, metals, glasses and graphite.

FIGS. 10A-C disclose a first expression of an embodiment of attaching a two part clamp pad 58a-b to a clamp member 56. In FIG. 10A, at least two slots 57a and 57b are shaped to accept two correspondingly shaped flanges 55a and 55'. In this example, T-slot 57a accepts a corresponding T-flange 55a of clamp pad 58a, and wedge-shaped slot 57' accepts a corresponding wedge-shaped flange 55' of clamp pad 58b.

Figure 11E:
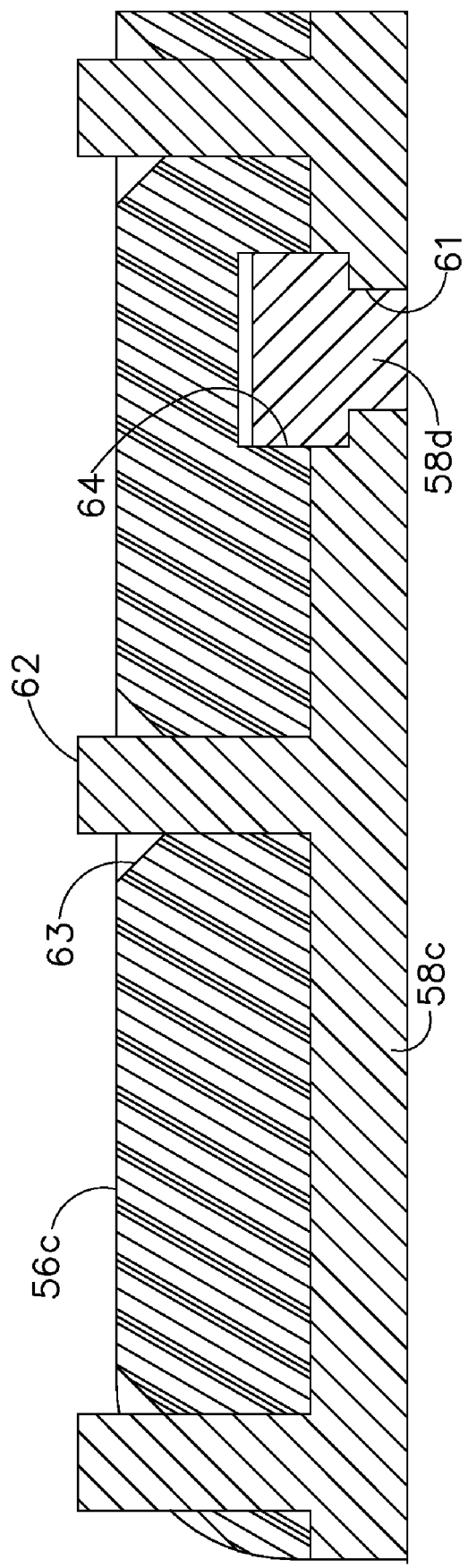
FIG. 11E is a cut-away view of an assembled clamp arm and tissue pad assembly of FIGS. 11A-D

FIGS. 11A-E illustrate a second expression of attaching a clamp pad 58c to a clamp arm 56c. Clamp pad 58c comprises one or more protrusions 62 for insertion into one or more corresponding apertures 63 in clamp arm 56c. If a second or more clamp pad(s) 58d is also used in accordance with the previous discussion, then clamp pad 58c further comprises corresponding aperture 61 for accepting one or more clamp pad(s) 58d. Clamp arm 56c has corresponding aperture(s) 63 for accepting protrusions 62, as well as a corresponding cavity 64 for accepting the one or more clamp pad 58d. FIG. 11E illustrates the components assembled together prior to staking. Clamp pad 58d fits inside the aperture 61 and cavity 64, and pad 58c is aligned with clamp arm 56c so that protrusions 62 align with chamfered aperture 63. Protrusions 62 have additional height beyond the top surface of clamp arm 56c to provide additional material to fill the chamfered volume during staking. Heat is applied to protrusions 62 above the clamp arm 56c; the protrusions deform and take the shape of the chamfered volume.

Figure 12A:
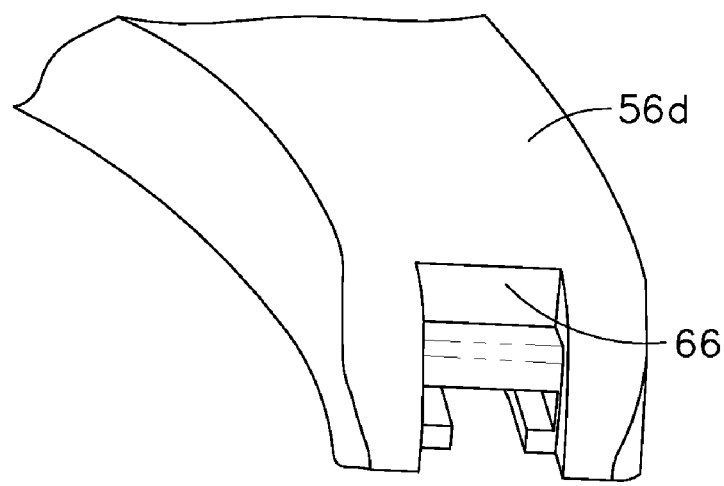
FIG. 12A is a perspective view of an alternate embodiment of a clamp arm having a distal connection point.
Figure 12B:
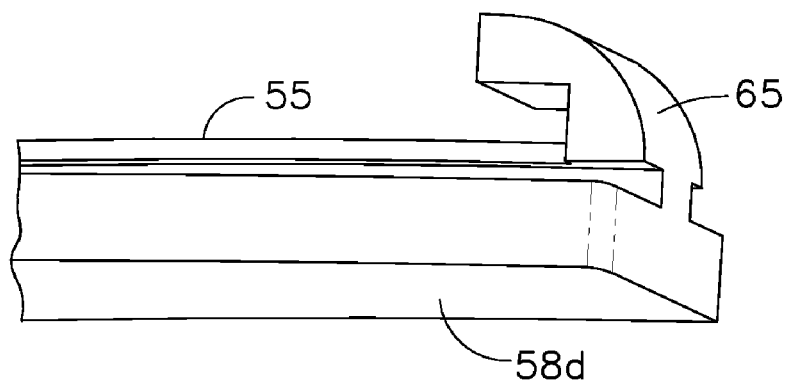
FIG. 12B is a perspective view of an alternate embodiment of a tissue pad having a distal connection member.
Figure 12C:
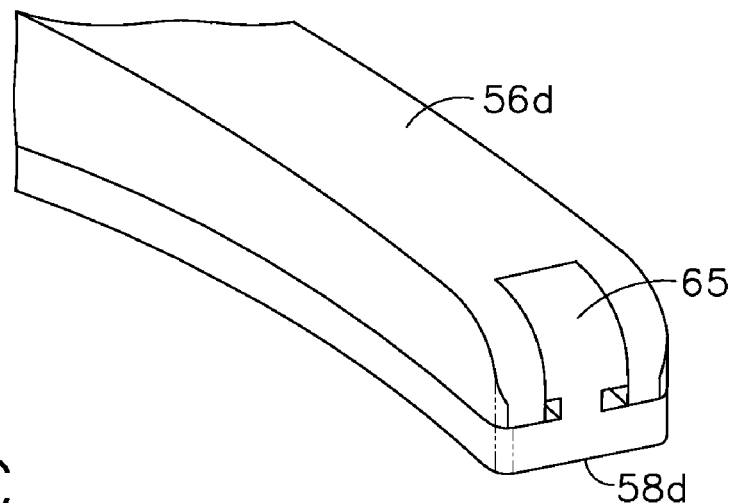
FIG. 12C is a perspective view of an assembled clamp arm and tissue pad of FIGS. 12A-B.

FIGS. 12A-C illustrate a third expression of attaching a clamp pad 58d to a clamp arm 56d. In addition to a T-shaped flange 55, clamp pad 58d further comprises a hook-like protrusion or clip 65 for attaching to a corresponding opening 66 at the distal tip of clamp arm 56d. In this expression, the distal tip of clamp arm 56d is open and the clamp pad 58d is inserted from the distal to proximal direction until the hook clip engages opening 66. Hook clip 65 may be biased closed so when clip 65 engages opening 66, clip 65 applies compressive forces against opening 66.

A first expression for a method for inserting a clamp pad on a clamp arm includes a) inserting a first clamp pad having a first width dimension greater than a second width dimension and having a first-shaped flange into a clamp arm having a slot that accepts the first-shaped flange; and b) engaging a pad stop to secure the clamp pad within the clamp arm. In a second expression of the method, the clamp pad consists of a second clamp pad fabricated from a base material and at least one filler material, which is a different material from the base material. The second clamp pad may have a second-shaped flange for engaging a second-shaped slot on the clamp arm. The tissue surfaces of the clamp pads may be smooth or have tissue gripping features, such as a saw-tooth configuration.

A first expression for a method for replacing clamp pads would include the steps of: a) disengaging a pad stop; b) removing a first clamp pad from the clamp arm; c) removing a second clamp pad from the clamp arm, wherein at least one of the first or second clamp pads has a first width dimension greater than a second width dimension; d) inserting third and fourth clamp pads into the clamp arm wherein at least one of the third or fourth clamp pads has a first width dimension greater than a second width dimension ; and e) engaging a pad stop to secure the third and fourth clamp pads within the clamp arm. In a second expression of this method one of the third and fourth clamp pads may be fabricated from a polymeric material such as TEFLON, and the other clamp pad may be fabricated from a base material and at least one filler material, which is a different material from the base material.

The tissue surfaces of the clamp pads may be smooth or have tissue gripping features, such as a saw-tooth configuration.

Figure 13:
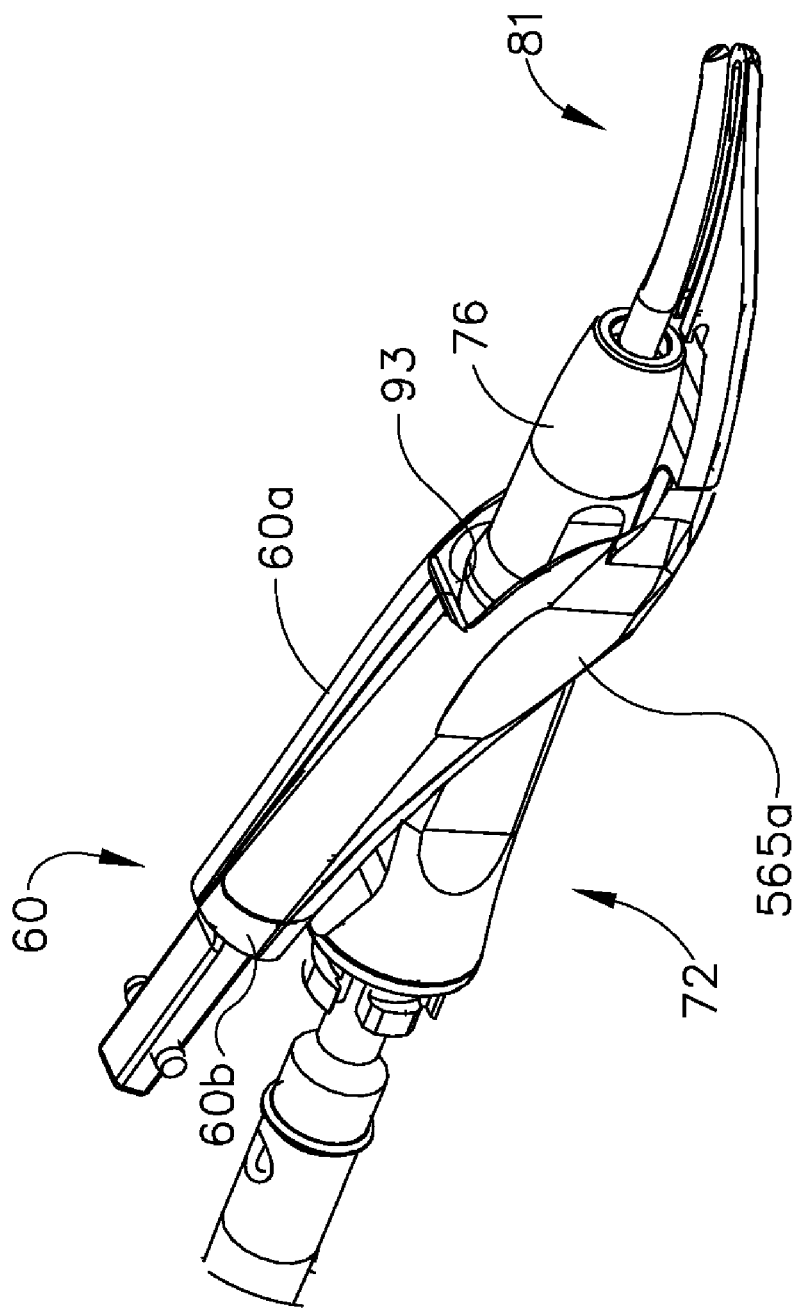
FIG. 13 is a partial view of the distal end of the ultrasonic instrument in accordance with the present invention.
Figure 14:
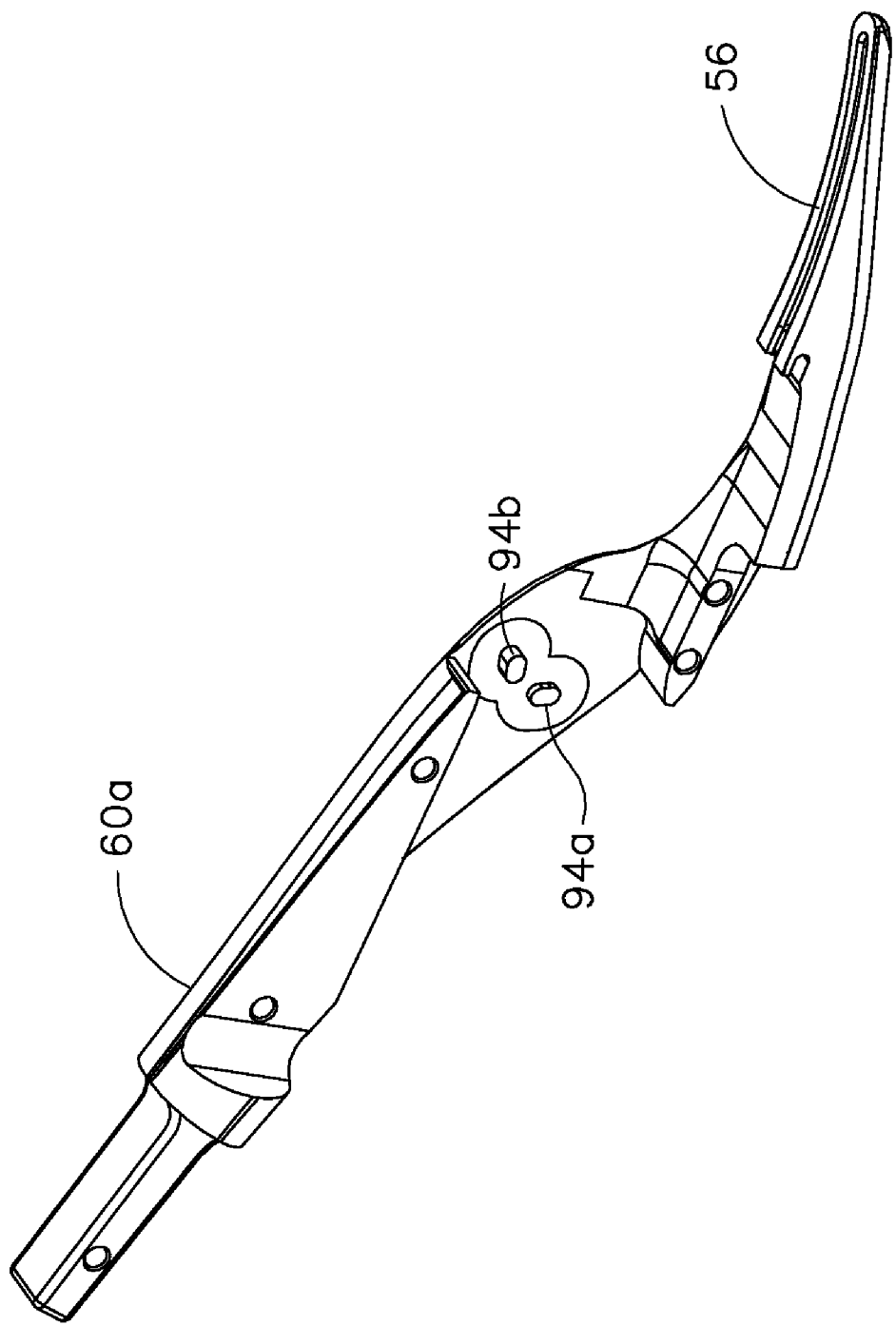
FIG. 14 is an exploded elevation view of one part of the clamp arm and clamp member and cam members.

Referring to FIGS. 13-15, a clamp arm 60 is configured for use with the present ultrasonic surgical instrument 100 and for cooperative action with blade 79 and clamp member 56. The clamp arm 60 is rotatably mounted to the distal end of outer shroud 72, detailed below, and connectably attaches at the distal end of thumb ring or actuation member 34. Clamp pad 58 mounts on the clamp member 56 for cooperation with blade 79, with rotational movement of the clamp arm 60 positioning the clamp pad in substantially parallel relationship to, and in contact with, blade 79, thereby defining a tissue treatment region. By this construction, tissue is grasped between clamp pad 58 and blade 79. Pivotal movement of the clamp member 56 with respect to blade 79 is affected by the provision of a pair of camming members on the clamp arm 60 that interface with the outer shroud 72. The outer shroud 72 is grounded to handle 68.

A first expression of clamp arm 60 comprises jaw-carrying member 60a and mating member 60b. Jaw-carrying member 60a includes two camming members 94a and 94b for mating with two corresponding camming slots 95a and 95b located outer shroud 72. Mating member 60b includes two camming members 96a and 96b for mating with two corresponding camming slots 97a and 97b located outer shroud 72. Corresponding camming members 94a/94b and 96a/96b (and corresponding camming slots 95a/95b and 97a/97b) may align along common axes perpendicular to the longitudinal axis of waveguide 80 or camming members may be offset to facilitate the assembly process. Members 60a and 60b fixedly attach to each other as shown in FIG. 13 to form clamp arm 60 via press fit or snap fit. Other attaching methods are available as is known to those skilled in the art, such as welding, glue, screwing, etc. Once assembled, clamp arm 60 defines an opening 93 for receiving outer shroud 72 and the interlocking of the respective cam members and cam slots. Alternatively, members 60a and 60b may be assembly around outer shroud 72 and all three elements mated together in one operation. One benefit of the cam open and closure mechanism is that it can provide both a rotational motion and linear motion of the clamp arm 60 and clamp member 56 thereby providing better control of the pressure profile between clamp pad 58 and blade 79.

In a second expression of clamp arm 60, the camming members may be replaced with spherical elements that interface with cam slots. Alternatively camming members may be replaced with spherical depressions for receiving ball bearings that interface with the cam slots. Other camming mechanism would be useful as is well known to the skilled artisan.

With solid camming members and corresponding slots, the force delivered between the clamp pad 58 and blade 79 is directly related to the force that the user applies at the thumb ring 35 and finger ring 36. In a third expression of clamp arm 60, a force limiting element 98, such as an elastomer or coil or leaf spring, may be inserted within one or more cam slots and provide a force limit to the coaptation force seen at the end effector 81. Preferably, the spring constant of an elastomer or spring ranges from 10-500 lb./in.

Outer shroud 72, distal shroud 76 and clamp arm 60 may be constructed from any number of biocompatible materials, such as titanium, stainless steel or plastics. Preferably, however, these elements are constructed of either 7075 or 6061 T6 aluminum. The aluminum provides a large benefit in terms of heat dissipation. Devices of the prior art have sheaths and clamp arms made of stainless steel. Typical values for thermal conductivity for aluminum are around 250 W/m K. The values for stainless steel are around 16 W/m K. Thus, aluminum has approximately 15 times greater capability to transmit heat through the same amount of volume.

The inventors have found through testing of similar inputs (clamp force and blade displacement), the present invention operates approximately 150° F. lower in temperature than instruments of the prior art. The aluminum components more effectively draw the heat away from the pad and the blade, thus keeping the end effector cooler than other prior art instruments.

Referring now to FIGS. 1, 2 and 16A-G housing 68 includes a proximal end, a distal end, and a cavity 59 extending longitudinally therein. Cavity 59 is configured to accept a switch assembly 300 and the transducer assembly 50.

In one expression of the current embodiment, the distal end of transducer 50 threadedly attaches to the proximal end of transmission rod 80. The distal end of transducer 50 also interfaces with switch assembly 300 to provide the surgeon with finger-activated controls on surgical instrument 19.

Transducer 50 includes a first conductive ring 400 and a second conductive ring 410 which are securely disposed within the transducer body 50 as is described in co-pending application Ser. No. 11/545,784.

Switch assembly 300 comprises a pushbutton assembly 310, a flex circuit assembly 330, a switch housing 350, a first pin conductor 360 and a second pin conductor 370. Switch housing 350 is saddle-shaped and is supported within handle assembly 68 by way of corresponding supporting mounts on switch housing 350 and housing portions 69 and 70. Housing 350 defines a first receiving area 353 for a dome switch, and a second receiving area 351 for a dome switch.

Figure 16B:
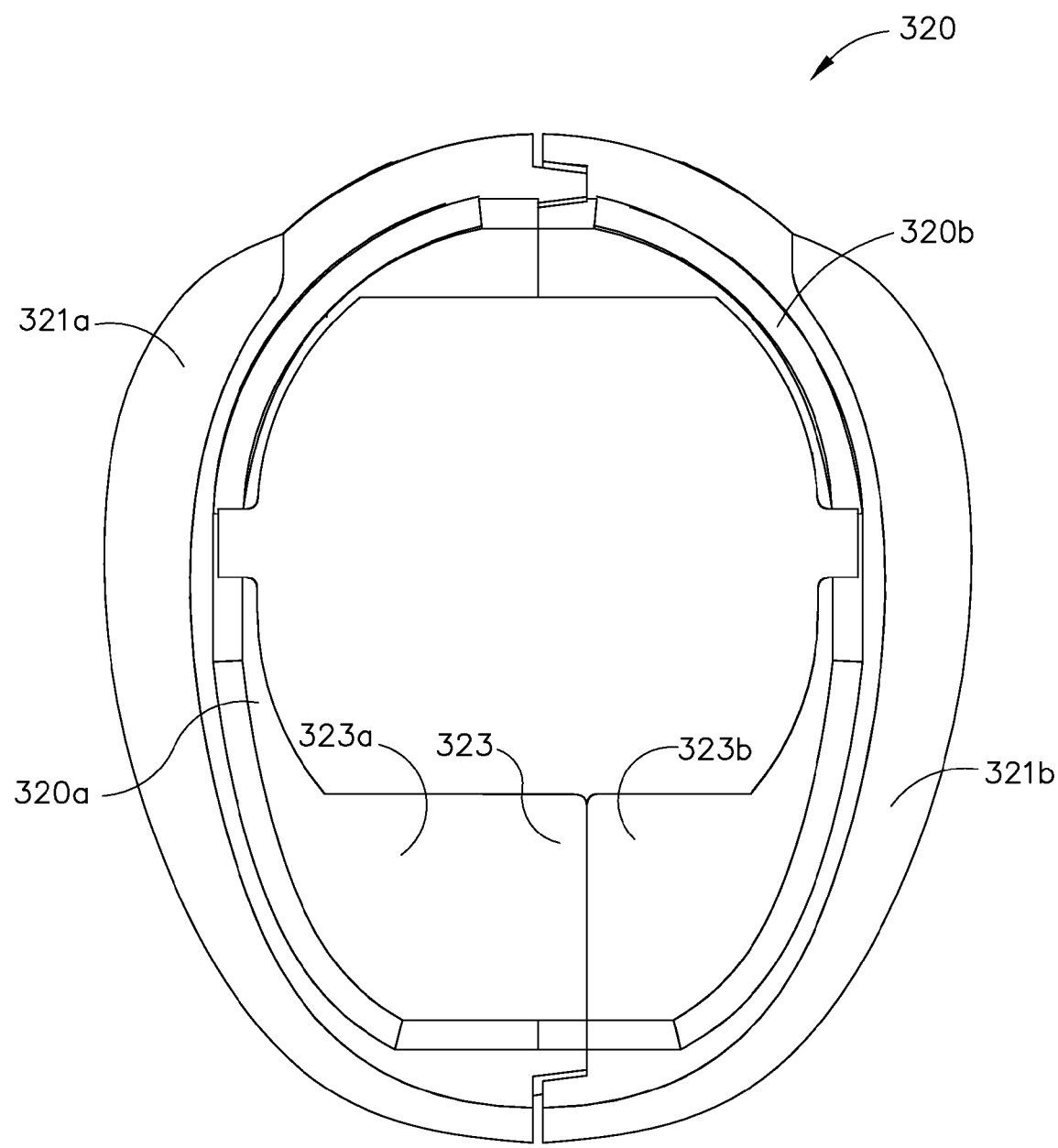
FIG. 16B is an elevation view of the two piece assembly of a push button in accordance with the present invention.
Figure 16C:
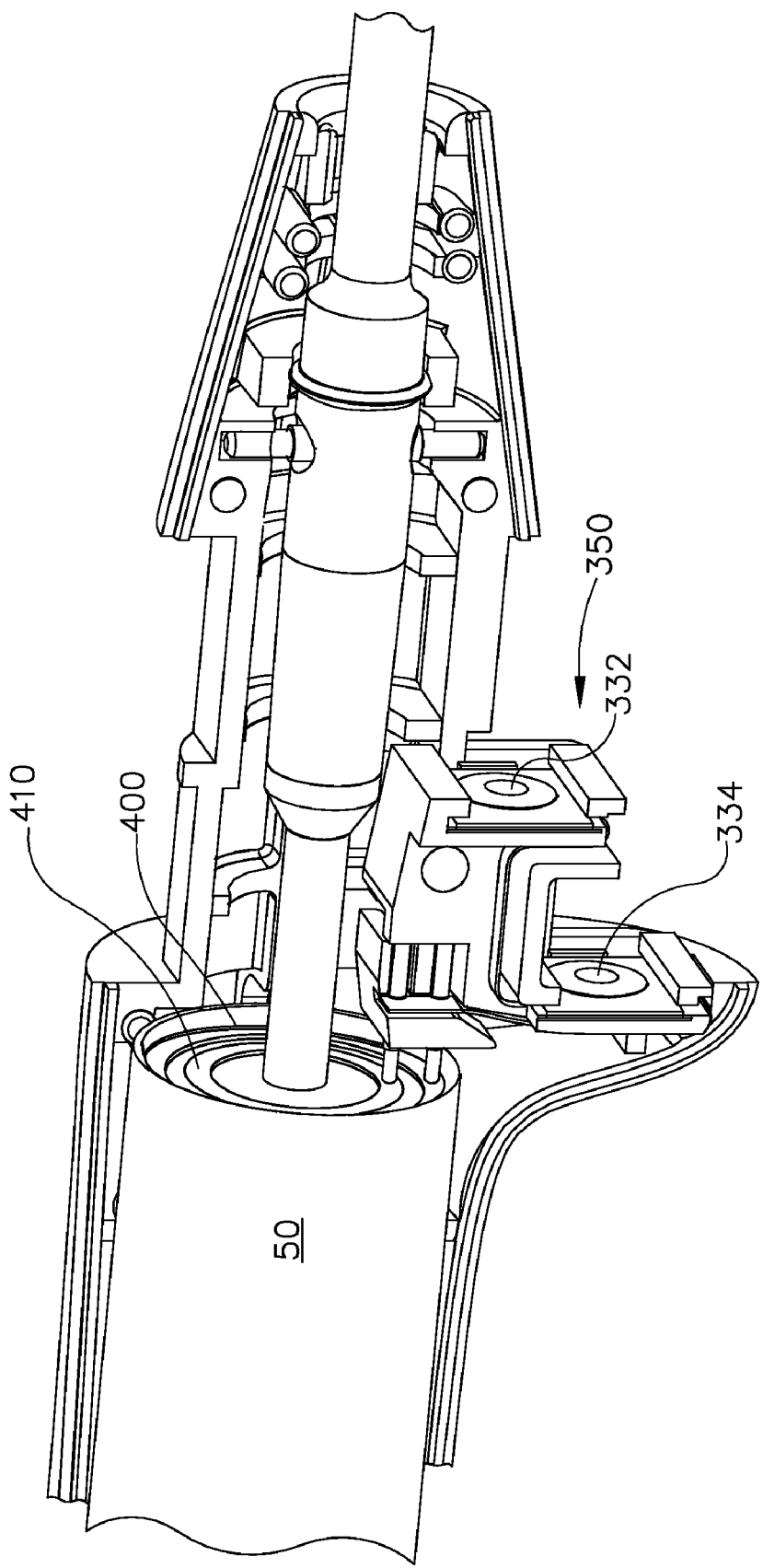
FIG. 16C is a cut-away elevation view showing the interface among the switch housing, transducer, waveguide and housing.
Figure 16D:
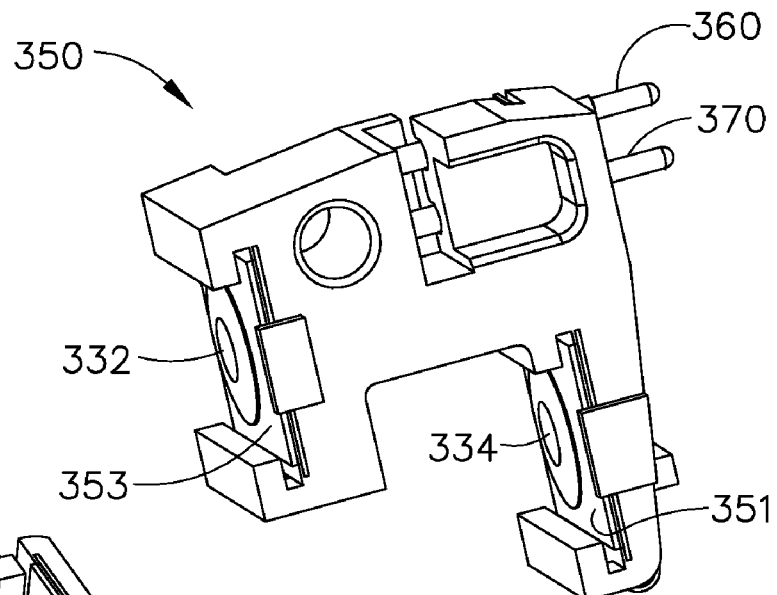
FIG. 16D is a perspective elevation view of a switch housing in accordance with the present invention.
Figure 16E:
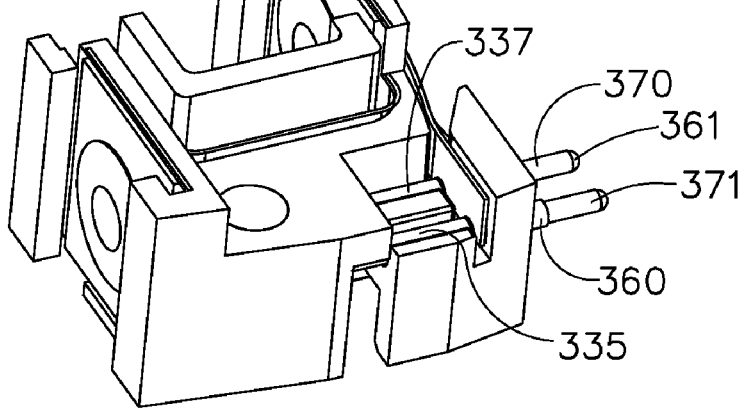
FIG. 16E is an alternate view of the switch housing of FIG. 16D.
Figure 16F:
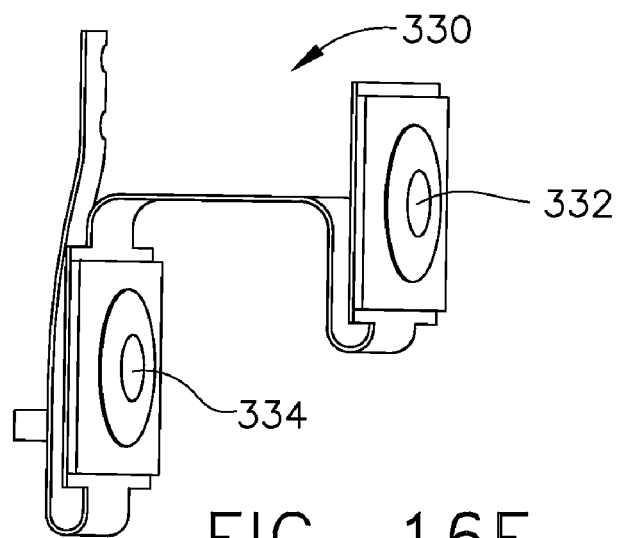
FIG. 16F is a view of a flex circuit in accordance with the present invention.

With particular reference now to FIGS. 16D and E, pins 360 and 370 are electrically connected to dome switch 332 and 334 via conductors 337 and 335, respectively, at one end and to the distal end of transducer 50 at a second end. Pins 360 and 370 each have a spring-loaded tip 361 and 371 that interface with transducer 50 as shown in FIG. 16C. Each end 361 and 371 have a 0.050 inch working travel to allow for manufacturing tolerances associated with the stackup of the assembled parts. Slidably attached to housing 68 are two triggers 320 and 322, each comprising first and second halves 320a, 320a and 322a, 322b, respectively. Shown in FIG. 16B is trigger 320, which comprises ridges 321a and b and contact surface 323 (made up of mating surfaces 323a and 323b). When assembled, triggers 320 and 322 (comprising contact surface 325, not shown) slidably attach to housing 68 and contact surfaces 323 and 325 mechanically engage dome switches 332 and 334, respectively. Ridges 321 and 326 provide interface between the user and triggers 320 and 322. Ridges 321 and 326 are designed to provide as much surface area for the user to depress in order to activate the instrument.

In a second expression of switch assembly 300 elastomeric connectors having copper traces etched onto the elastomer press fit into switch housing 350 to provide the electrical interconnect between transducer 50 and flex circuit 330. One end of the elastomer connectors electrically engage dome switches 332 and 334 via conductors 337 and 335. The other end of the elastomer connectors slidably interface with conductors 400 and 410 of transducer 50. Compression of the elastomer connectors allow a working travel of up to 20% of the total height of the elastomer connectors to allow for manufacturing tolerances associated with the stackup of the assembled parts.

A flex circuit 330 provides for the electromechanical interface between pushbuttons 321 and 322 and the generator 30 via transducer 50. Flex circuit comprises two dome switches 332 and 334 that are mechanically actuated by depressing pushbuttons 321 or 322 axially in the x direction. Dome switches 332 and 334 are electrical contact switches, that when depressed provide an electrical signal to generator 30 as shown by the electrical wiring schematic of FIG. 16G. Flex circuit 330 also comprises two diodes within a diode package 336 and conductors, 335 and 337 as is known to those in the art, that connect to pins 360 and 370, respectively, which in turn provide electrical contact to ring conductors 400 and 410, which in turn are connected to conductors in cable 22 that connect to generator 30.

Flex circuit 330 generally sits within a channel 352 of switch assembly 350 so that dome switches 332 and 334 interface with the corresponding backing surfaces 351 and 353. Backing surfaces provide a firm support for the dome switches during operation, discussed below. Dome switches 332 and 334 may be fixedly attached to backing surfaces 351 and 353 by any convenient method, such as, an adhesive.

Figure 16G:
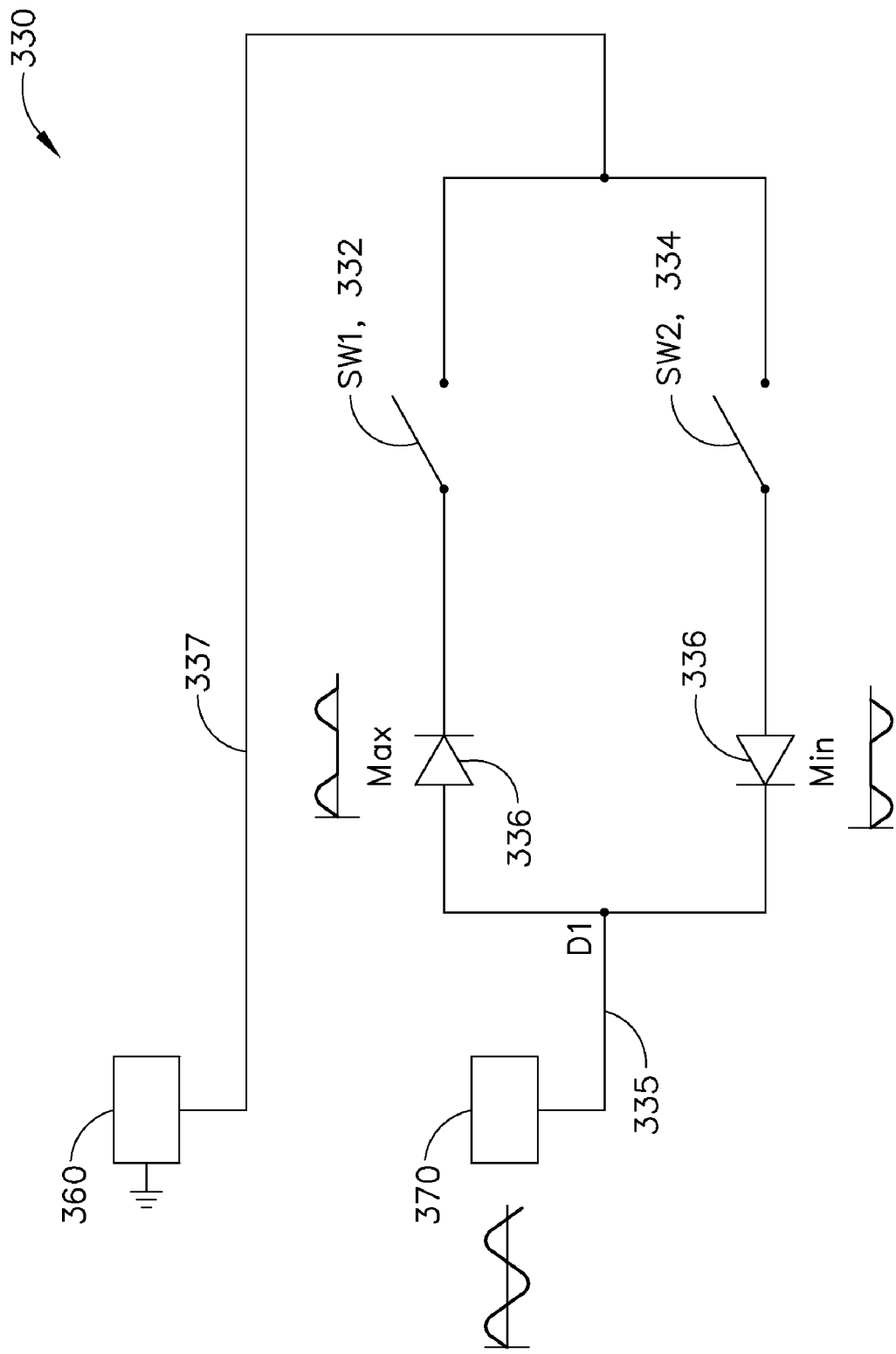
FIG. 16G is an electrical schematic of the hand switch circuit.
Figure 16H:
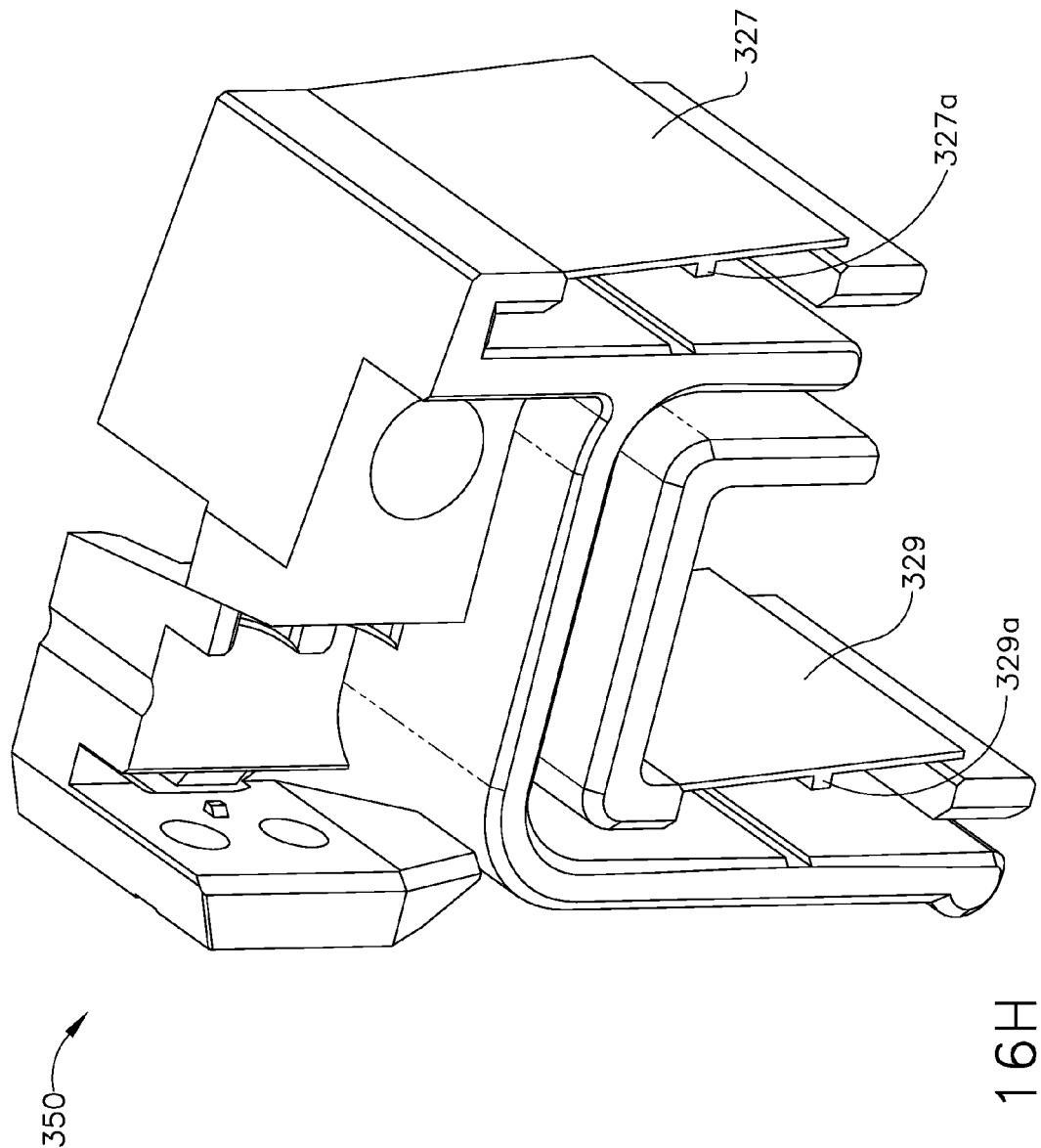
FIG. 16H is an alternate embodiment of the switch housing and actuation.

As is readily apparent, by depressing pushbuttons 321 and 322 the corresponding contact surfaces 323 and 324 depress against corresponding dome switches 332 and 334 to activate the circuit illustrated in FIG. 16G. When the surgeon depresses 321 pushbutton, the generator will respond with a certain energy level, such as a maximum ("max") power setting; when the surgeon depresses pushbutton 322, the generator will respond with a certain energy level, such as a minimum ("min") power setting, which conforms to accepted industry practice for pushbutton location and the corresponding power setting.

In an alternate expression contact surfaces 323 and 325 contact a living hinge 327 and 329, respectively. Each living hinge comprises an actuator 327a and 329a, which preferably extend across the width of the living hinge. The living hinge 327 and 329 help eliminate assembly tolerance variations and any significant amount of "play" in the triggers that rattle when the instrument is handled and apply a slight pre-load to the triggers that in turn can eliminate any "play". The living hinge 327 and 329 further provide a more pronounced tactile feel of the triggers since the actuators 327a 329a hit the respective dome switch 332 and 334 of the flex circuit in an optimum location.

Figure 17A:
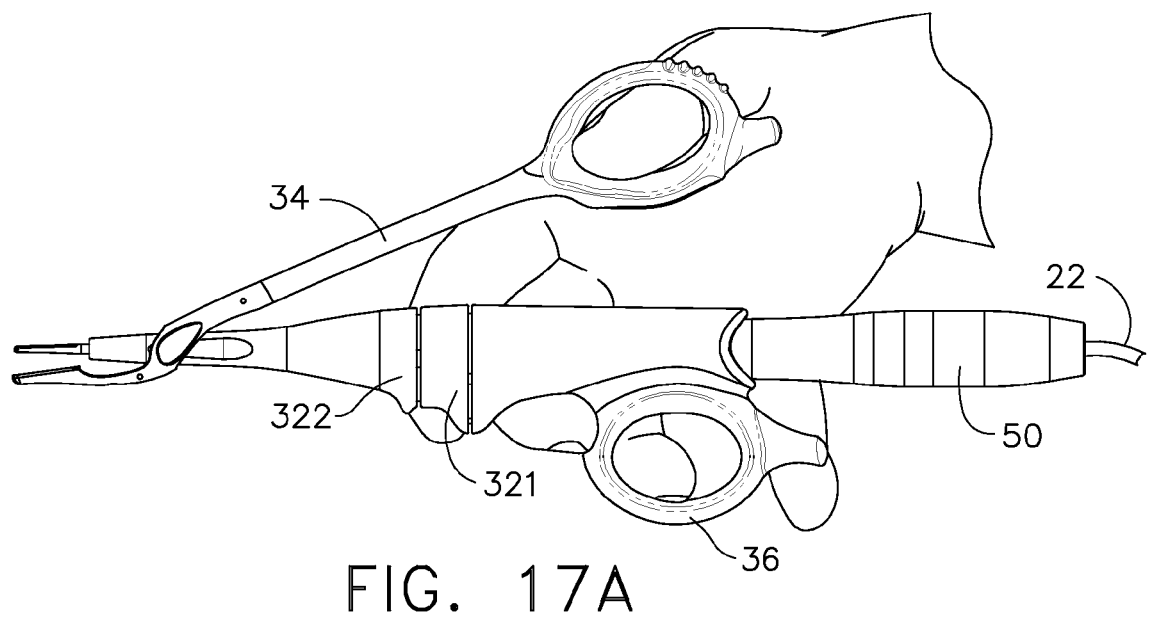
FIG. 17A is an elevation view of an ultrasonic instrument in accordance with the present invention as may be grasped by a user.
Figure 17B:
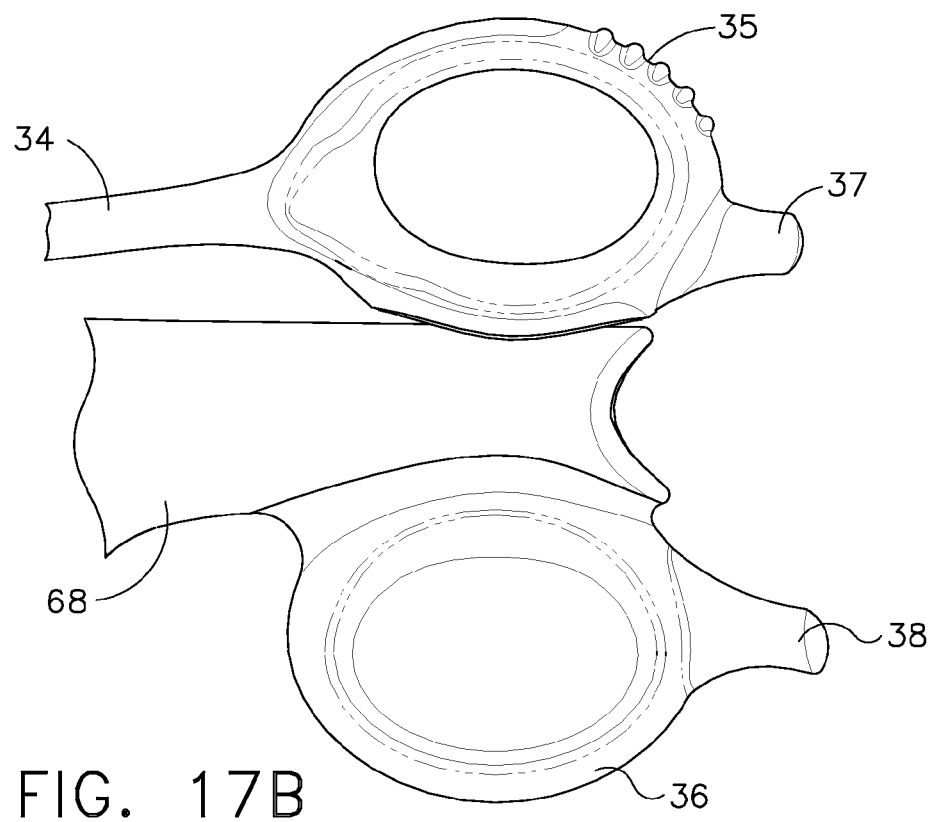
FIG. 17B is an exploded view of the finger and thumb interface of a ultrasonic instrument in accordance with the present invention.
Figure 19A:
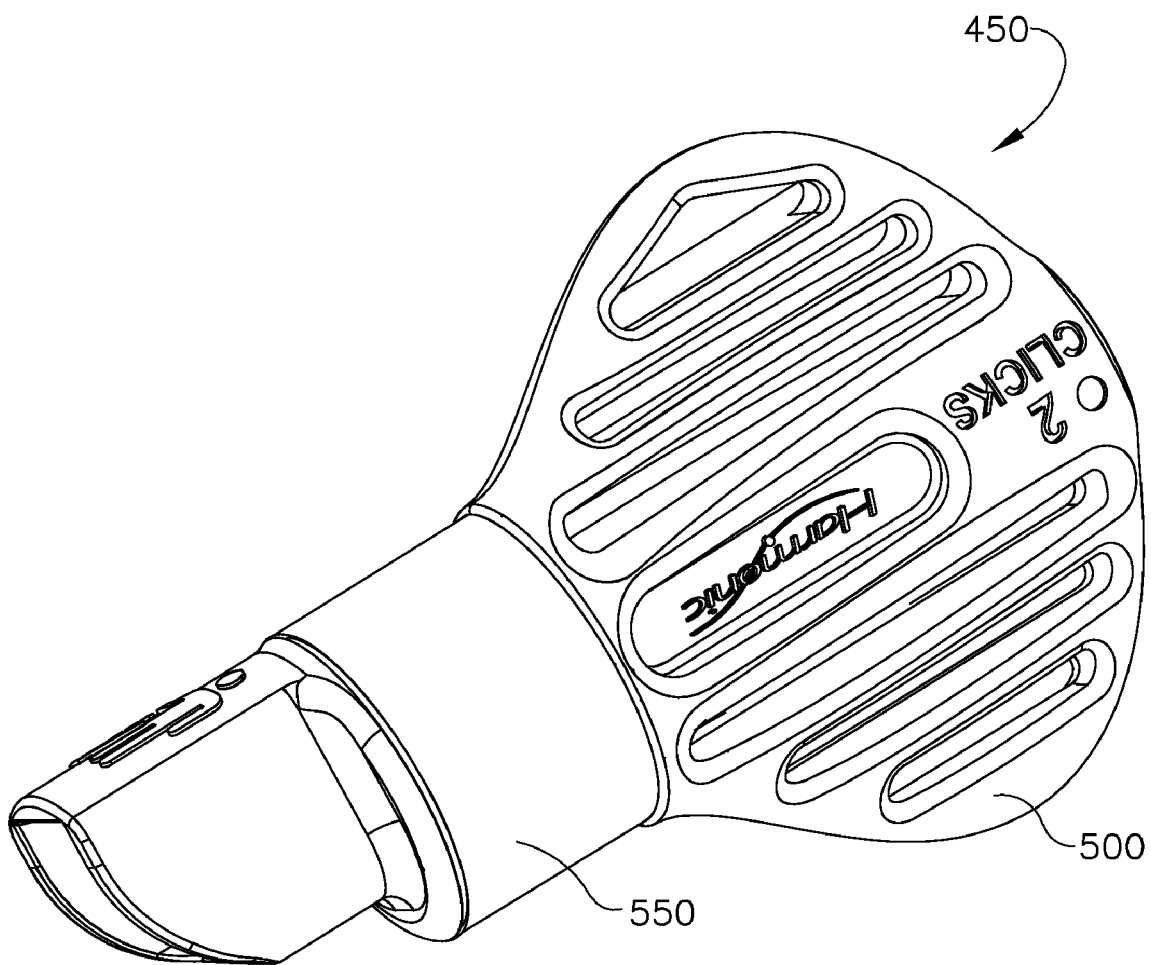
FIG. 19A is a perspective view of a two-piece torque wrench in accordance with the present invention.
Figure 19B:
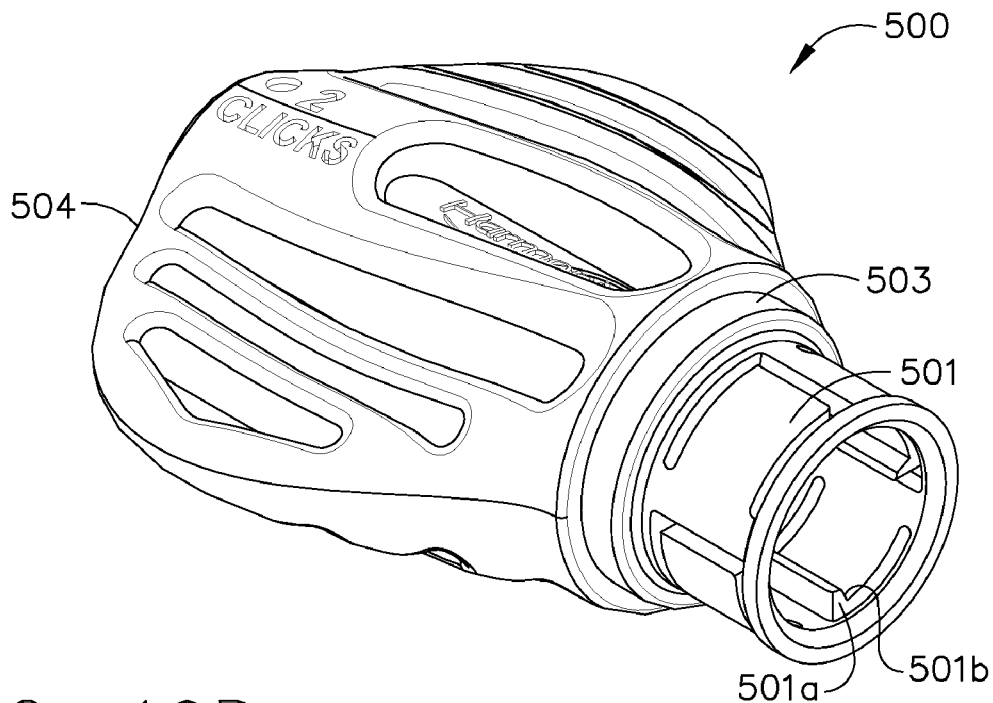
FIG. 19B is a perspective view of a hand wrench in accordance with the present invention.
Figure 19C:
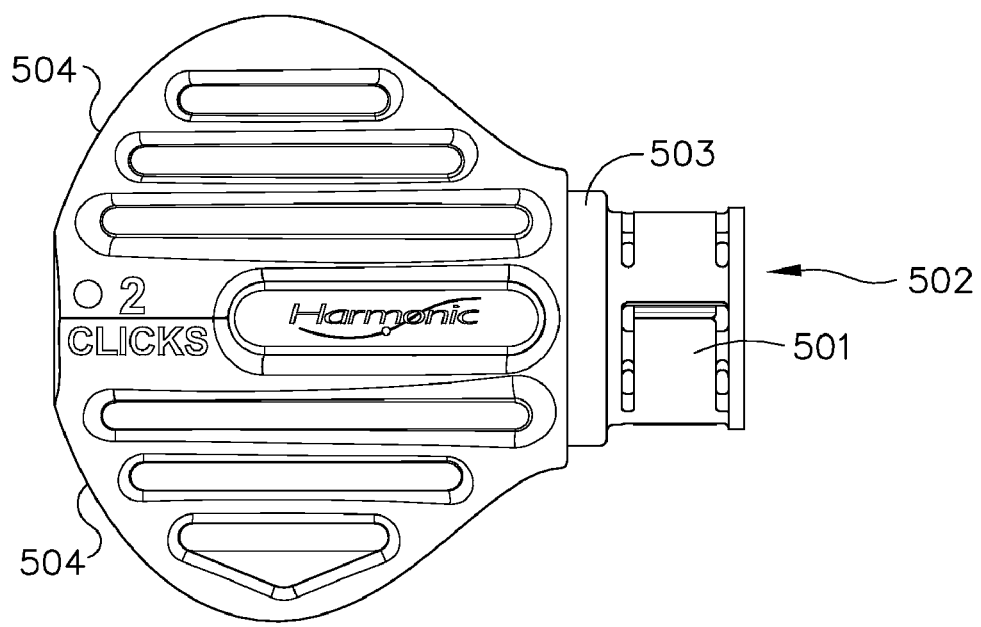
FIG. 19C is an elevation view of the hand wrench of FIG. 19B.
Figure 19D:
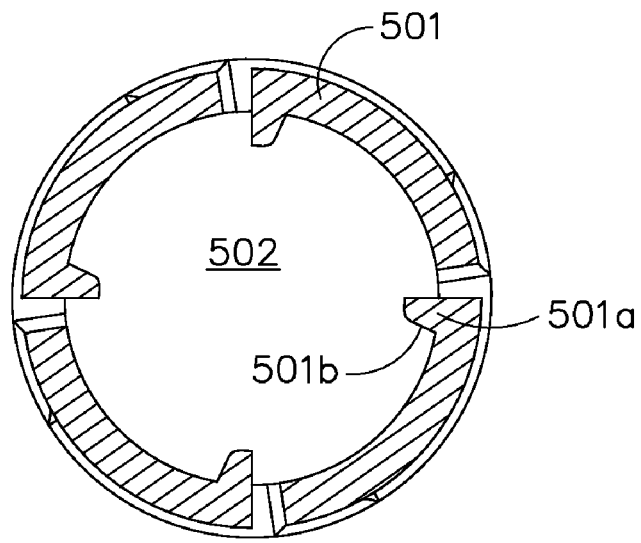
FIG. 19D is a cross sectional end view of the distal end of a hand wrench depicting cantilever arm and teeth geometry.
Figure 19E:
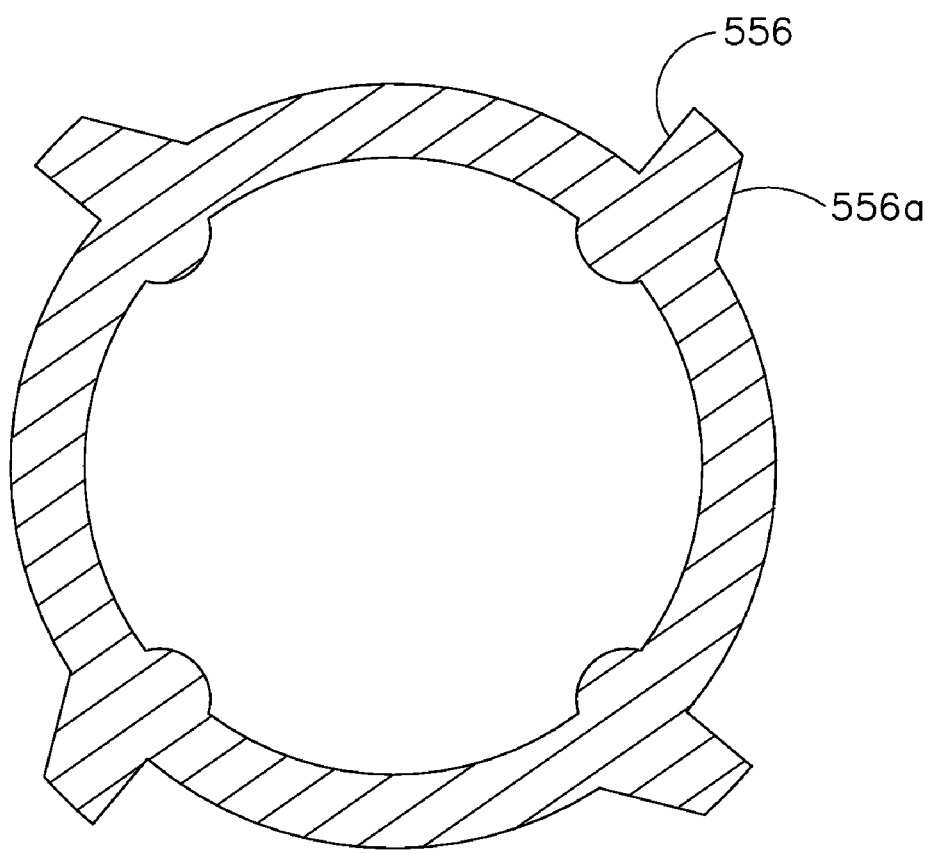
FIG. 19E is a cross sectional view of an adaptor depicting spline gear geometry.
Figure 19F:
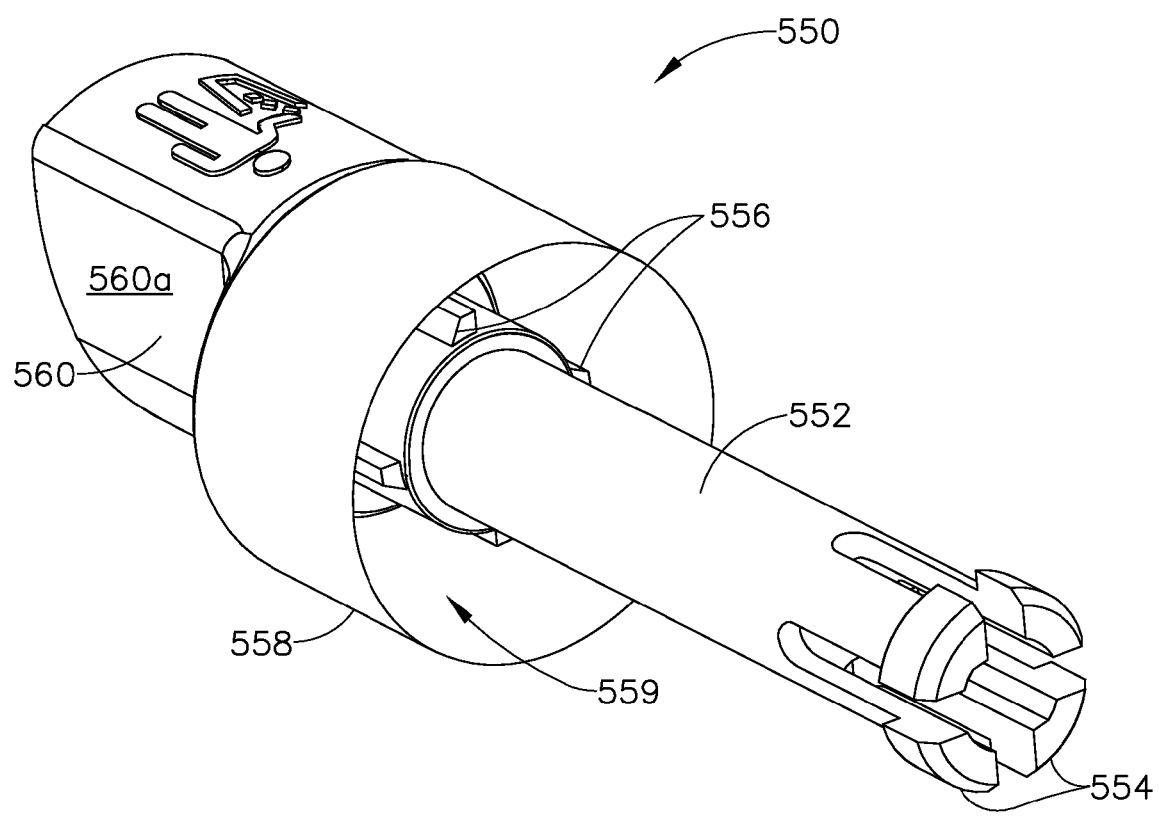
FIG. 19F is a perspective view of an adaptor for use with a hand wrench in accordance with the present invention.
Figure 19G:
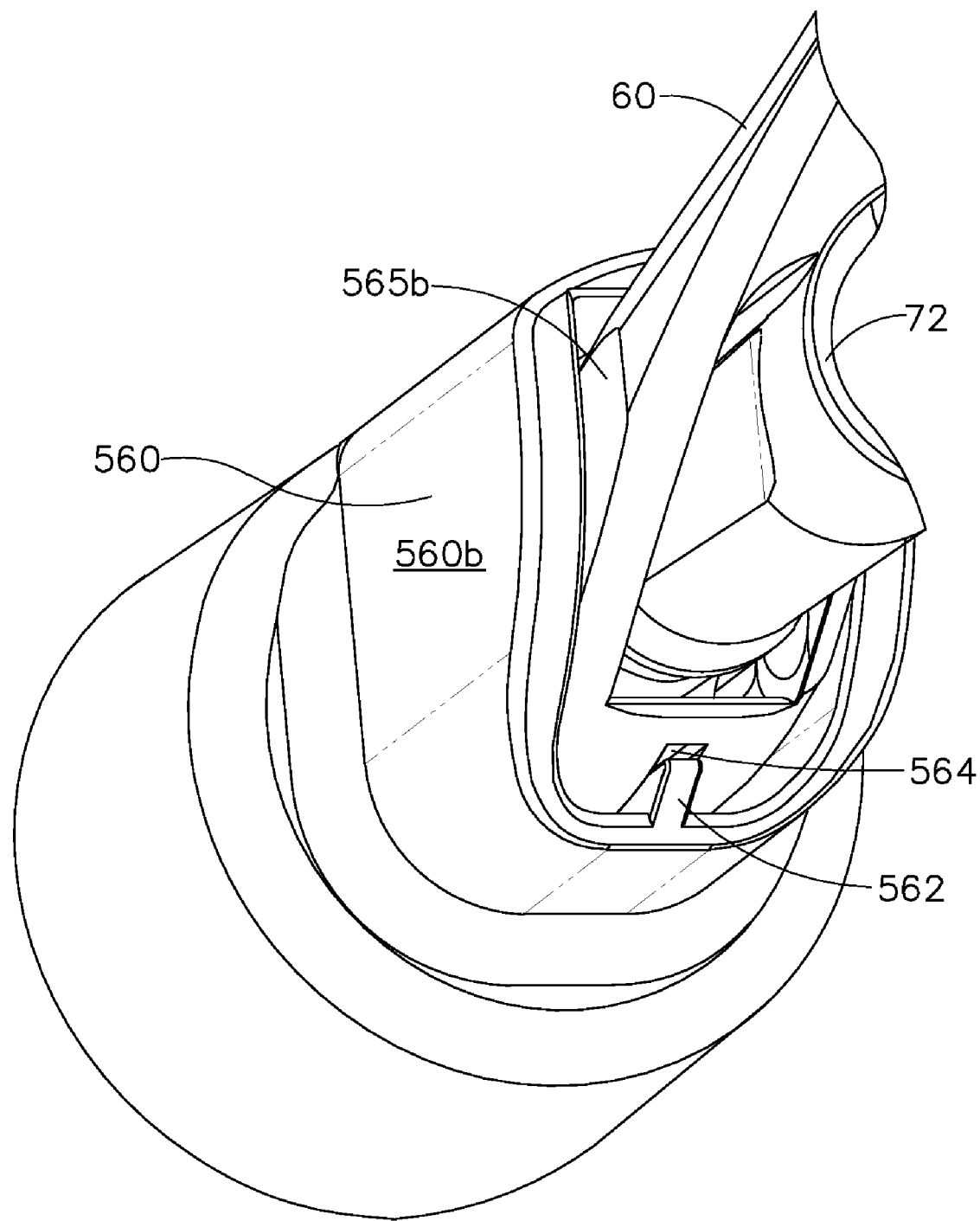
FIG. 19G is a partial perspective view of a hand wrench interfacing with an ultrasonic instrument in accordance with the present invention.

Referring now to FIGS. 17A-B, the pushbutton axial actuation reduces stress on the surgeon's fingers and allows the fingers to actuate force in a more ergonomic position preventing stresses at the hands and wrists. The switch movement also allows comfortable button activation in less than optimal hand positions, which surgeons often encounter throughout a typical procedure.

At the proximal end of each access ring 35 and 36 are protrusions 37 and 38, respectively, that allow the surgeon to rest his or her pinky finger for added control and comfort. This also allows the surgeon to use the pinky when clamping on tissue, thereby reducing the force on the other fingers. Each access ring 35 and 36 includes a soft-touch surface on the interior and exterior surfaces whether by inserting fingers into the access rings or palming the access rings. This feature allows a greater number of hand sizes to comfortably use the device.

Referring to FIG. 18, access rings 35 and 36 define a length L. Preferably, the center of gravity of the surgical instrument 100 in combination with the transducer 50 is positioned within length L, more preferably within length L1, and most preferably within length L2. This position of the center of gravity allows the instrument to balance within the surgeon's hand to provide more precise control of the instrument and eliminate hand fatigue during procedures.

Referring now to FIGS. 18 and 19A-E, a two-piece torque wrench 450 is shown. The torque wrench includes a hand wrench 500 and an adaptor 550. In one embodiment, hand wrench 500 is provided with cantilever arms 501 disposed in an annular fashion about the centerline of hand wrench 500. Cantilever arms 501 include teeth 501a disposed, in one embodiment, in an inward perpendicular fashion in relation to cantilever arms 501. Teeth 501a, in one embodiment of the current invention, are disposed with a cam ramp 501b at a 25° angle with respect to the perpendicular angle between arm 501 and teeth 501a. Lumen 502 extends the entire length of hand wrench 500 for accepting adaptor 550.

Adaptor 550 has a longitudinal shaft 552 with cantilevered tabs 554 at its distal end. At the proximal end of shaft 552 are spline gears 556 projecting in a perpendicular fashion along the outer circumference of shaft 552. Spline gears 556 include cam ramps 556a disposed at an angle from about 23° to about 28° with respect to the perpendicular angle between the outer circumference of shaft 552 and spline gears 556. Shaft 552 further defines a lateral opening (not shown) proximal to spline gears 556 for accepting curved blade 79, discussed below. Adaptor further includes an interface 560 rigidly connected to shaft 552 and defining an opening for rigidly engaging the distal end of instrument 19. Optionally, a skirt 558 surrounds spline gears 556 to prevent glove snags due to moving parts and forms a cavity 559.

In assembly, torque wrench opening 502 is aligned with shaft 552 and guided along substantially the entire length of shaft 552 until the tabs 554 flex inward and capture shoulder 505 (not shown) at the distal end of hand wrench 500. Hand wrench lip 503 engages the distal end of optional skirt 558 allowing cantilever teeth 501a to slidably engage spline gears 556. Cam ramp 501b slidably engages retainer cam ramps 29b. The torque wrench assembly 450 slidably engages the distal end of instrument 19 and is held rigidly in place. Flat surfaces 560b and 560a of interface 560 mate with flat surfaces 565b (FIG. 18) and 565a (not shown) at the distal end of activation member 34 (clamp arm 60) and rail 562 slidably engaging slot 564 on clamp arm 60 and distra shroud 76 and outer shroud 72 all provide structural support to maintain adapter 550 firmly engaged with instrument 19.

Clockwise annular motion or torque is imparted to hand wrench 500 through paddles 504. The torque is transmitted through arms 501 and teeth 501a to gears 556, which in turn transmit the torque to the waveguide 80 via clamp arm assembly 60 via outer shroud 72 via insulated pin 27. When a user imparts 5-12 lbs. of torque, the ramps 501b and 556 cause the arms 501 to move or flex away from the centerline of wrench 500 ensuring that the user does not over-tighten the waveguide 80 onto transducer 50. When a counter-clockwise torque is applied to wrench 500 via paddles 504, the perpendicular flat sides of teeth 501a and 556 abut allowing a user to impart a torque to the interface between the waveguide 80 and transducer 50 in proportion to the force applied to the paddles facilitating removal of the instrument 100 from the transducer 50. The torque wrench 450 may be constructed from a durable plastic, such as polycarbonate or a liquid crystal polymer. It is also contemplated that the wrench 450 may alternatively be made from a variety of materials including other plastics, ceramics or metals.

In another embodiment (not shown), the paddles and cantilever arm assembly may be separate components attached by mechanical means or chemical means such as adhesives or glue.

Preferably, the ultrasonic clamp coagulator apparatus 19 described above will be processed before surgery. First, a new or used ultrasonic clamp coagulator apparatus is obtained and if necessary cleaned. The ultrasonic clamp coagulator apparatus can then be sterilized. In one sterilization technique the ultrasonic clamp coagulator apparatus is placed in a closed and sealed container, such as a plastic or TYVEK bag. Optionally, the ultrasonic clamp coagulator apparatus can be bundled in the container as a kit with other components, including a torque wrench 450. The container and ultrasonic clamp coagulator apparatus, as well as any other components, are then placed in a field of radiation that can penetrate the container, such as gamma radiation, x-rays, or high-energy electrons. The radiation kills bacteria on the ultrasonic clamp coagulator apparatus and in the container. The sterilized ultrasonic clamp coagulator apparatus can then be stored in the sterile container. The sealed container keeps the ultrasonic clamp coagulator apparatus sterile until it is opened in the medical facility.

Figure 20:
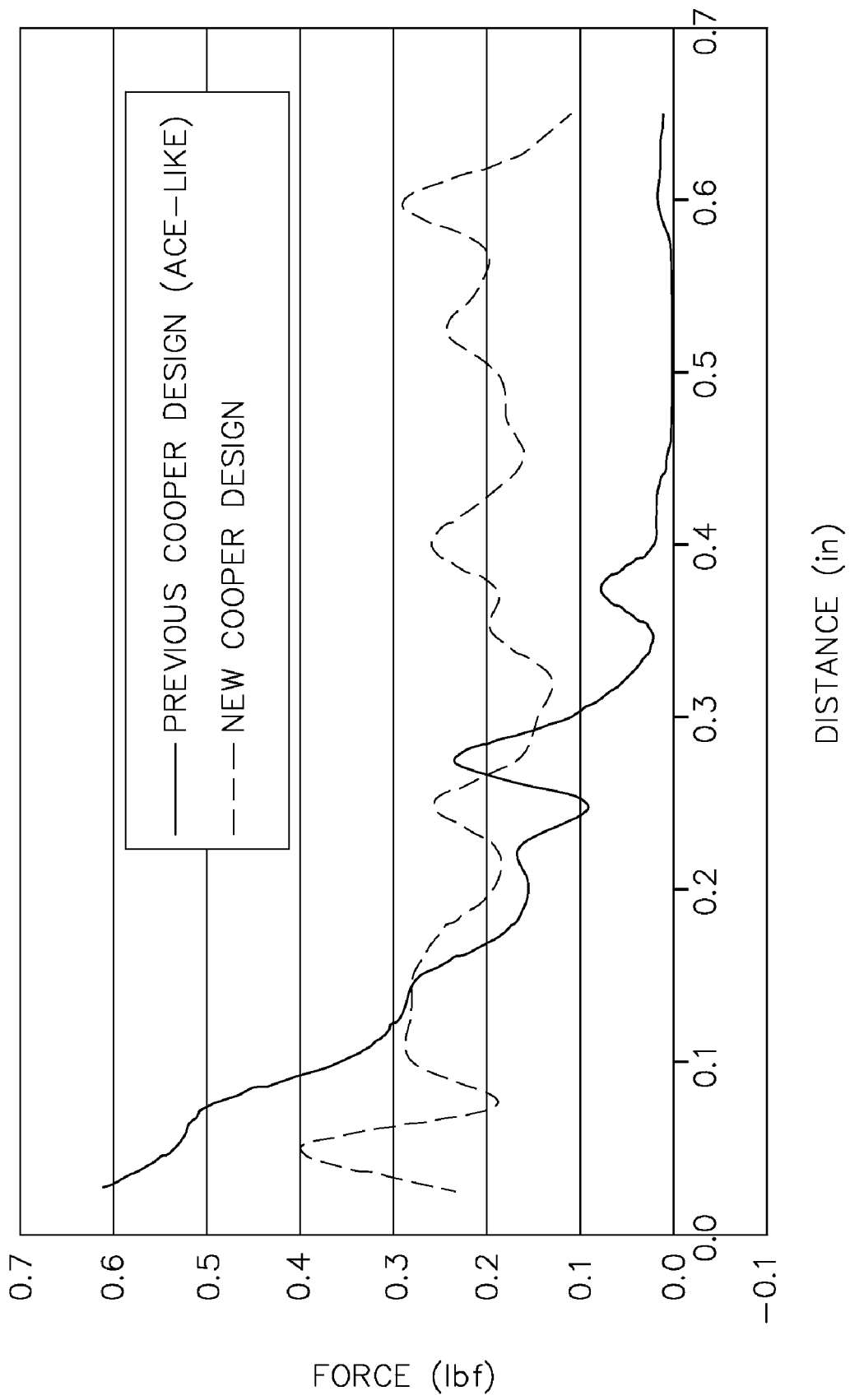
FIG. 20 is a graph illustrating the pressure profile across the blade in accordance with the present invention relative to the prior art.
Figure 21:
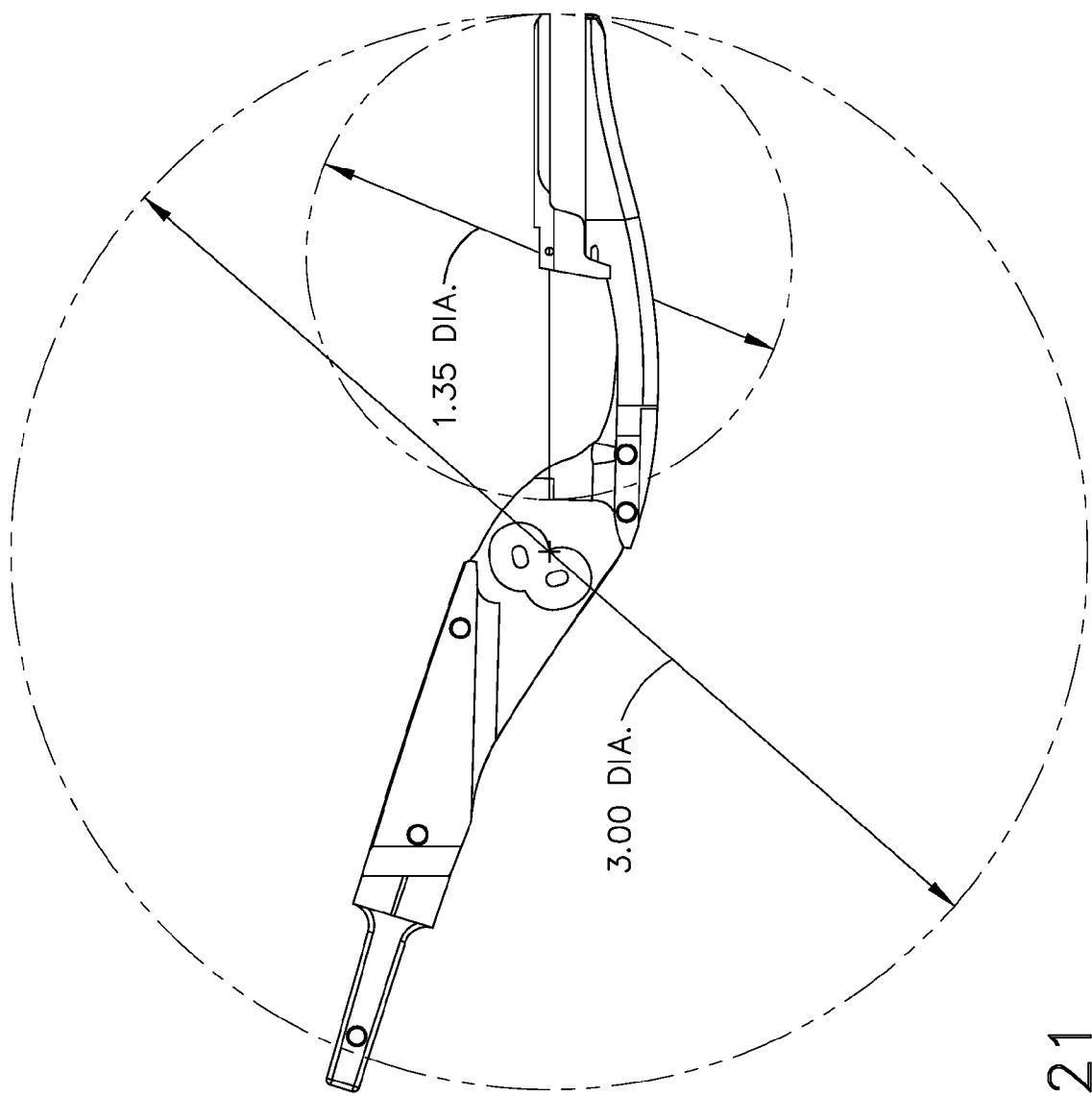
FIG. 21 is a graphical illustration of the pivot radius in accordance with the present invention.

Referring now to FIGS. 20 and 21 the present invention enables a more even pressure profile across the blade from the proximal end to the distal end as compared to the prior art. An even pressure profile along the blade provides simultaneous tissue transaction along the blade as well as excellent cutting at the tip of the blade. The even pressure profile is accomplished by creating as close a parallel closure of the clamp pad against the blade as possible.

The pivot radius of the prior art is less than 1.0 inches and in some cases less than 0.75 inches. In accordance with the present invention, the pivot radius is increased to be over two times the pivot radius of the prior art. In one preferred embodiment, the pivot radius is equal to 1.5 inches. The pivot radius is not limited to this dimension and exact dimensions are left to the design artisian. What is important, however, is that as the clamp arm is moved through its pivot radius the clamp arm exhibits a substantially parallel closure with respect to the blade. Parallel closure means that as the clamp pad closes against the blade, a substantially equal pressure is exerted across the blade from the proximal end to the distal end. Parallel closure allows for less variation in pressure profile across the blade from the proximal end to the distal end. In one example the pressure profile ranges from about 0.1 lbs. measured at the distal tip to about 0.4 lbs. measured proximal of the distal tip, but most notably only ranging between 0.1 lbs. at the distal tip and less than 0.3 lbs. across substantially the entire length of the blade as shown in FIG. 20.

The present invention further comprises a displacement limited force application, whereas prior art instruments comprise a force limiting element, such as a spring, that limits the amount of force applied to the blade by the clamp arm. In accordance with the present invention actuation member 34 deflects as increased load is applied. The force delivered to the tissue is dependent upon the length of actuation member 34, the cross sectional area, the modulus of elasticity and the amount of deflection allowed before it hits a hard stop on the shroud.

As actuation member 34 deflects and load is applied to blade 79, the blade 79 deflects as well. Thus, the clamp force system is comprised of two members: the inherent stiffness of actuation member 34 (mainly comprised of blade deflection and distal seal compression); and the blade side stiffness (mainly comprised of actuation member 34 and thumb ring stiffness). These two stiffnesses can be calculated, measured and used to predict and manipulate clamp force. In one preferred embodiment, the actuation member 34 has a stiffness of approximately 3 lb/in. to about 7 lb/in., and the blade 79 has a stiffness of between 150 lb/in and about 250 lb/in.

Further, the thumb ring height gap G shown in FIG. 16A defines the compression length of the actuation member 34 side of the spring system. Height G preferably ranges from about 0.15 inches to about 0.33 inches.

One benefit of the displacement force limiting system is increased pad life. As the device is used, the pad wears and a groove begins to form. This is prevalent in the abuse case where the device is activated when fully closed with no tissue present between blade 79 and clamp pad 58. In prior art ultrasonic instruments, when the groove became deeper, a very similar amount of force was placed on the blade due to the force limiting spring. The slope of the force vs. displacement curve is relatively flat.

In the present invention, however, as the pad wears, the thumb ring only rotates slightly downward due to the deflection of the lever system after thumb ring 35 bottoms out at handle 68 (distance G). Since there is less distance for the thumb ring to travel, the force on the blade decreases. The present invention has a steeper force vs. displacement curve resulting in a larger drop in force due to pad wear. Thus, the pad groove does not increase as readily as the prior art and the instrument still performs as needed with lower forces dues to pad wear.

Figure 22:
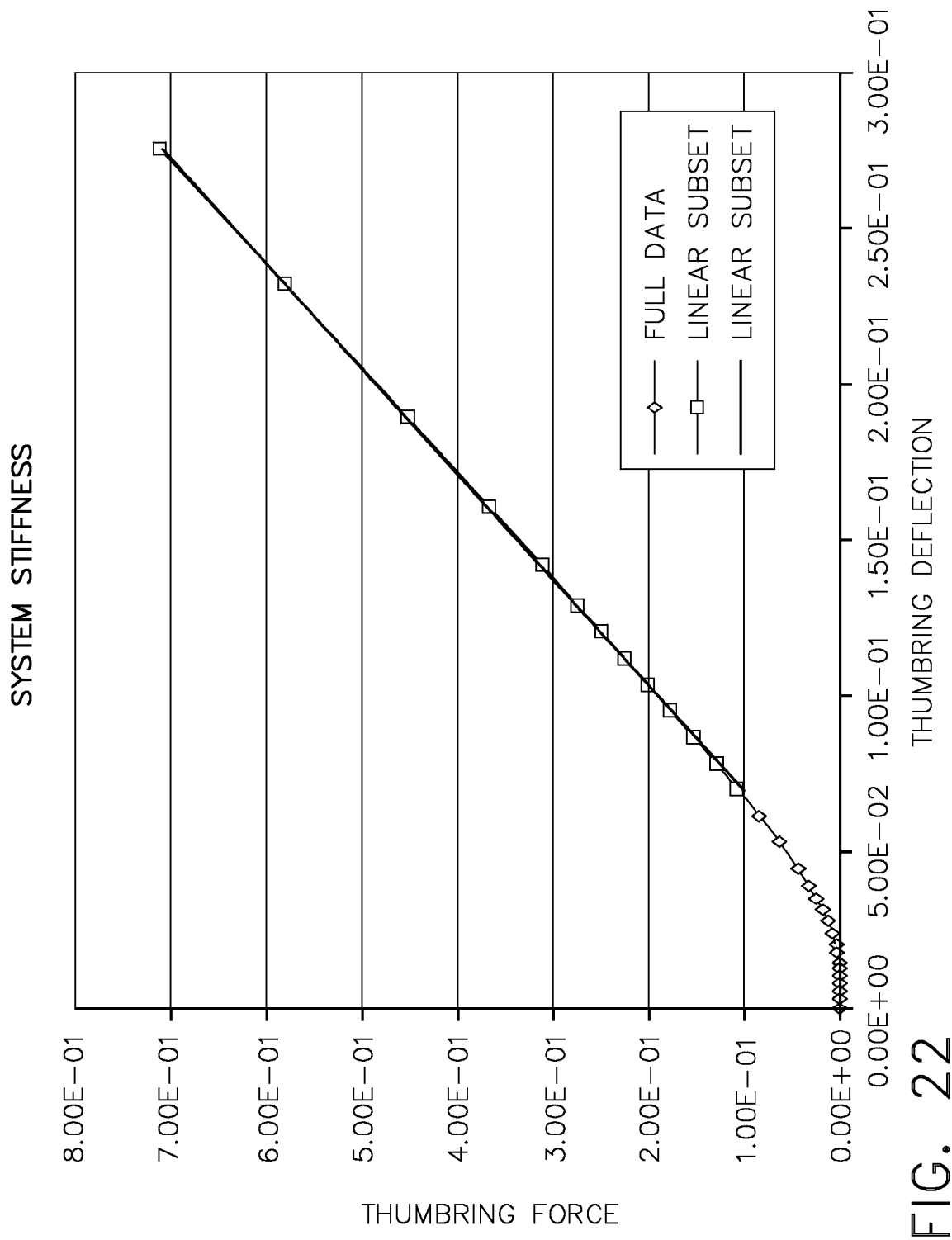
FIG. 22 is a graph illustrating thumb ring displacement vs. thumb ring force in accordance with one embodiment of the present invention.

Referring to FIG. 22, the graph illustrates one embodiment of the representative stiffness of the present invention. The y-axis is the force the user exerts on the thumb ring and the y-axis is the thumb ring deflection. The stiffness is approximately 3 lbs/in.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. Moreover, the structure of each element associated with the present invention can be alternatively described as a means for providing the function performed by the element. Accordingly, it is intended that the invention be limited only by the spirit and scope of the appended claims.

We claim:

1. An ultrasonic surgical instrument comprising:
   a housing having a proximal end and a distal end;
   a first shroud having a distal end and a proximal end joined to the housing distal end, the first shroud defining a longitudinal axis and having an inner diameter from about 0.175 inches to about 0.22 inches;
   a second shroud having a distal end and a proximal end joined to the distal end of the first shroud, and aligned with the longitudinal axis; wherein an inner diameter of the second shroud is from about 0.185 inches to about 0.20 inches; and
   an ultrasonic waveguide positioned within the first and second shroud and having a proximal end, a distal end and an ultrasonically actuated blade positioned at the distal end of the waveguide.

2. The ultrasonic surgical instrument of claim 1, wherein the length of the first shroud is from about 1.5 inches to about 2.4 inches.

3. The ultrasonic surgical instrument of claim 1, wherein the waveguide comprises an overmold having an outer diameter and positioned at a distal node.

4. The ultrasonic surgical instrument of claim 3, wherein the second shroud has an inner diameter less than the outer diameter of the overmold.

5. The ultrasonic surgical instrument of claim 1, wherein the length of the second shroud is from about 0.600 inches to about 0.650 inches.

6. A method of assembling an ultrasonic instrument of claim 1 comprising the steps of:
   a) securing the proximal end of the waveguide within the housing;
   b) sliding the first shroud over the waveguide;
   c) sliding the second shroud the waveguide;
   d) securing the proximal end of the first shroud to the distal end of the housing; and
   e) securing the proximal end of the second shroud to the distal end of the first shroud.

7. A method of assembling an ultrasonic instrument of claim 1 comprising the steps of:
   a) securing the proximal end of the waveguide within the housing;
   b) securing the proximal end of the first shroud to the distal end of the housing; and
   c) securing the proximal end of the second shroud to the distal end of the first shroud.

8. An ultrasonic surgical instrument comprising:
   a housing having a proximal end and a distal end;
   a first shroud having a proximal end joined to the housing distal end and a distal end, the first shroud defining a longitudinal axis and having an inner diameter from about 0.175 inches to about 0.22 inches and wherein the first shroud distal end and proximal end define a length from about 1.5 inches to about 2.4 inches;
   a second shroud having a proximal end joined to the distal end of the first shroud, and aligned with the longitudinal axis and having an inner diameter from about 0.185 inches to about 0.20 inches and wherein the second shroud distal end and proximal end define a length from about 0.600 inches to about 0.650 inches; and
   an ultrasonic waveguide positioned within the first and second shroud and having a proximal end, a distal end and an ultrasonically actuated blade positioned at the distal end of the waveguide.

* * * * *